US009340607B2

(12) United States Patent
Ravetch et al.

(10) Patent No.: US 9,340,607 B2
(45) Date of Patent: *May 17, 2016

(54) ANITBODIES SPECIFIC FOR THE PROTOFIBRIL FORM OF BETA-AMYLOID PROTEIN

(71) Applicant: ROCKEFELLER UNIVERSITY (THE), New York, NY (US)

(72) Inventors: Jeffrey V. Ravetch, New York, NY (US); Hidehiro Fukuyama, Strasbourg (FR)

(73) Assignee: The Rockefeller University, New York, NY (US)

( * ) Notice: Subject to any disclaimer, the term of this patent is extended or adjusted under 35 U.S.C. 154(b) by 220 days.

This patent is subject to a terminal disclaimer.

(21) Appl. No.: 13/903,081

(22) Filed: May 28, 2013

(65) Prior Publication Data

US 2013/0315917 A1 Nov. 28, 2013

Related U.S. Application Data

(62) Division of application No. 12/738,955, filed as application No. PCT/US2008/083659 on Nov. 14, 2008, now Pat. No. 8,470,321.

(60) Provisional application No. 61/019,747, filed on Jan. 8, 2008, provisional application No. 60/988,481, filed on Nov. 16, 2007.

(51) Int. Cl.

| C07K 16/18 | (2006.01) |
|---|---|
| A61K 39/395 | (2006.01) |
| G01N 33/577 | (2006.01) |
| G01N 33/53 | (2006.01) |
| G01N 33/68 | (2006.01) |
| A61K 39/00 | (2006.01) |

(52) U.S. Cl.
CPC ............ *C07K 16/18* (2013.01); *G01N 33/6896* (2013.01); *A61K 2039/505* (2013.01); *C07K 2317/34* (2013.01); *C07K 2317/56* (2013.01); *C07K 2317/565* (2013.01); *G01N 2333/4709* (2013.01); *G01N 2800/2821* (2013.01)

(58) Field of Classification Search
CPC ............... C07K 2317/34; C07K 16/18; C07K 2317/76; C07K 2317/56; C07K 2317/565; C07K 2317/24; C07K 2316/96; G01N 33/6896; G01N 2333/4709; G01N 2800/28; G01N 2800/2814; G01N 2800/2821; A61K 2039/505; A61K 39/3955
See application file for complete search history.

(56) References Cited

U.S. PATENT DOCUMENTS

| 5,869,620 | A | 2/1999 | Whitlow et al. |
| 6,372,215 | B1 | 4/2002 | Starling et al. |
| 6,919,075 | B1 | 7/2005 | Solomon et al. |
| 7,195,761 | B2 | 3/2007 | Holtzman et al. |
| 8,470,321 | B2 | 6/2013 | Ravetch et al. |
| 2002/0192750 | A1 | 12/2002 | Fox et al. |
| 2004/0043935 | A1 | 3/2004 | Frangione et al. |
| 2004/0223970 | A1 | 11/2004 | Afar et al. |
| 2005/0255102 | A1 | 11/2005 | Violette et al. |
| 2006/0280733 | A1 | 12/2006 | Kayed et al. |
| 2007/0110750 | A1 | 5/2007 | Glabe et al. |

FOREIGN PATENT DOCUMENTS

| WO | 9843089 A1 | 10/1998 |
| WO | 02/46237 A2 | 6/2002 |
| WO | 0246237 A2 | 6/2002 |
| WO | 03080672 A1 | 10/2003 |
| WO | 2004024090 A2 | 3/2004 |
| WO | 2005011599 A2 | 2/2005 |
| WO | 2005123775 A1 | 12/2005 |
| WO | 2006081171 A1 | 8/2006 |
| WO | 2006083533 A2 | 8/2006 |
| WO | 2007064972 A2 | 6/2007 |
| WO | 2007108756 A1 | 9/2007 |
| WO | 2008156622 A1 | 12/2008 |
| WO | 2010130946 A1 | 11/2010 |

OTHER PUBLICATIONS

Szabo P et al. (2008) Natural human antibodies to amyloid beta peptide. Autoimmunity Rev. 7:415-420.*
Harrington CR et al. (1993) Characterisation of an epitope specific to the neuron-specific isoform of human enolase recognised by a monoclonal antibody raised against a synthetic peptide corresponding to the C-terminus of beta/A4-protein. Biochimica et Biophysica Acta, 1158:120-128.*
Solomon et al., "Monoclonal antibodies inhibit in vitro fibrillar aggregation of the Alzheimer β-amyloid peptide," P.N.A.S. (1996):93:452-455.
McLaurin et al, "Therapeutically effective antibodies against amyloid-β peptide target amyloid-β residues 4-10 and inhibit cytotoxicity and fibrillogenesis," Nature Medicine (2002):8:1263-1269.

(Continued)

*Primary Examiner* — Kimberly A. Ballard
(74) *Attorney, Agent, or Firm* — Fox Rothschild LLP; Gerard P. Norton; Jianming Jimmy Hao

(57) ABSTRACT

Isolated antibodies have been characterized which show specific affinity to a repeating conformational epitope of a protofibril form of the human β-amyloid peptide as compare to low molecular weight forms of β-amyloid peptide. These isolated antibodies and related pharmaceutically effective compositions may be useful in the therapeutic and/or prophylactic treatment of Alzheimer's disease by effectively blocking the ability of the protofibril form of β-amyloid peptide to form fibril forms linked with complications associated with Alzheimer's disease. The isolated antibodies of the present invention are also useful in various diagnostic assays and associated kits.

17 Claims, 12 Drawing Sheets

(56) References Cited

OTHER PUBLICATIONS

Tamura et al., "Structural correlates of an anticarcinoma anitobyd: identification of specificity-determiing residues (SDRs) and development of a minimally immunogenic antibody variant by retention of SDRs only," J. Immunol. (2000):164:1432-1441.

Alberts B et al., Molecular Biology of the Cell, Third Edition, Garland Publishing, New York, 1994, pp. 1216-1220.

Englund Hillevi et al., "Sensitive ELISA detection of amyloid-beta protofibrils in biological samples," Journal of Neurochemistry (Oct. 2007); 103(1):334-345.

International Preliminary Report on Patentability issued for PCT/US2008/083659.

Kayed et al., "Fibril specific, conformation dependent antibodies recognize a generic epitope common to amyloid fibrils and fibrillar oligomers that is absent in prefibrillar oligomers," Molecular Neurodegeneration (2007): vol. 2, No. 18, pp. 1-11.

Kuby J., Immunology, Third Edition W.H. Freeman & Co., New York, 1997, pp. 131-134.

Lambert et al., "Monoclonal antibodies that target pathological assemblies of A beta," Journal of Neurochemistry (Jan. 2007): 100(1):23-25.

Padlan EA et al, "Structure of an antibody-antigen complex; crystal structure of the HyHEL-10 Fab-lysozyme complex," Proc Natl Acad Sci USA, 1989; 86:5938-5942.

Paul, WE. Fundamental Immunology, Third Edition. Raven Press, New York, 1993, pp. 292-295.

Rudikoff et al., "Single amino acid substitution altering antigen-binding specificity," PNAS (Mar. 1982); vol. 79, pp. 1979-1983.

Schupf et al., "Peripheral abeta subspecies as risk biomarkers of alzheimer's disease," Proceedings of the National Academy of Sciences of the United States of America (2008; vol. 105, No. 37, pp. 14052-14057.

Mohajeri et al: "Assessment of the bioactivity of antibodies against beta-amyloid peptide in vitro and in vivo", Neurodegenerative Diseases, vol. 1, No. 4-5, Jan. 1, 2004, pp. 160-167, XP002509425.

\* cited by examiner

ANITBODIES SPECIFIC FOR THE PROTOFIBRIL FORM OF BETA-AMYLOID PROTEIN

CROSS-REFERENCE TO RELATED APPLICATIONS

This application is a Divisional of U.S. patent application Ser. No. 12/738,955 filed Apr. 20, 2010, which is a 371 National Phase Application of PCT/US08/83659 filed Nov. 14, 2008, which in turn claims priority to provisional patent applications Nos. 60/988,481 filed Nov. 16, 2007 and 61/019,747 filed Jan. 8, 2008. The contents of all applications are hereby incorporated by reference.

FIELD OF THE INVENTION

The present invention relates to isolated antibodies that interact specifically with conformational epitopes of a protofibril form of human beta-amyloid peptide. These antibodies show minimal or no detectable affinity towards lower molecular weight forms of beta-amyloid peptide. The antibodies disclosed herein will be useful in the diagnosis, treatment and/or prevention of beta-amyloid plaque deposition associated with the onset and progression of Alzheimer's disease.

BACKGROUND OF THE INVENTION

Beta-Amyloid (Aβ) peptides are thought to be a causative agent for Alzheimer's disease ("AD") through the formation of insoluble Aβ peptide fibrils and deposition of these fibrils to form amyloid plaques. The formation of such plaques within the area of the brain critical for memory and other cognitive functions is thought to lead to dementia associated with this disease (see Selkoe, 1994, *J. Neuropathol. Exp. Neurol.* 53:438-447). Beta-Amyloid peptides comprise a group of peptides 39-43 amino acids long that are proteolytically processed from amyloid precursor protein (APP), by both β-secretase and γ-secretase at the amino- and carboxyl-terminus, respectively. There are at least five distinct isoforms of APP: 563, 695, 714, 751, and 770 amino acids in length, respectively (see Wirak et al., 1991 *Science* 253:323). These isoforms of APP are generated by alternative splicing of primary transcripts of the APP gene. Numerous missense mutations have been identified in APP in families with autosomal dominant early-onset Alzheimer's disease. Some mutations cluster near the secretase cleavage sites and affect APP metabolism either by increasing the production or the proportion of Aβ forms (e.g., $A\beta_{42}$), which tends to be more fibrillogenic and to aggregate faster than other forms. Neuronal toxicity may reside in the large molecular weight fibrils which are formed via aggregation of soluble Aβ peptides into insoluble fibrils and, subsequently, fibril incorporation into amyloid plaques. An intermediate fibril form is the protofibril (PF) form, a large molecular weight oligomeric form of Aβ peptides which is soluble in vitro and may be isolated as an approximately ~670 kDa entity. Thus, the in vitro formation of insoluble Aβ peptide fibrils is the end result of the initial oligomerization of Aβ peptide to form a structurally distinct, soluble higher molecular weight protofibril form. These transient protofibrils structures are precursor to the amyloid fibers responsible for cell dysfunction and neuronal loss in Alzheimer's disease (AD) and other protein aggregation diseases.

Various treatments have been forwarded in attempts to prevent the formation of Aβ peptide, for example, inhibitors to prevent the proteolytic processing of APP. Also, immunotherapy strategies such as administration of anti-Aβ antibodies (to induce clearance of amyloid deposits) or immunization with Aβ peptide antigens (to promote a humoral response) have been enlisted in an attempt to reduce plaque size and density.

U.S. Pat. No. 7,179,463, issued to Lannfelt et al., discloses a method of treating Alzheimer's disease by administering an antibody raised against a protofibril consisting of the Arctic mutation within the Aβ peptide coding region. No exemplification of raised antibodies are presented in the specification and no comparison as to affinity for low molecular weight forms of Aβ peptide are presented.

U.S. Pat. Nos. 6,761,888 and 6,750,324, issued to Schenk et al., disclose a series of antibodies which recognize various epitopes along the amino acid sequence of $A\beta_{42}$. Antibodies specific for the N-terminus and mid-regions of $A\beta_{42}$ showed efficacy in reducing plaque both ex vivo and in vivo.

Despite current knowledge in the field of treating and preventing Alzheimer's disease, there remains a need for an improved compositions and methods of treating and/or preventing this disease. The compositions and methods of the present invention address and meet these needs by disclosing antibodies specific for protofibrillar forms of Aβ peptide while showing minimal detectable affinity against low molecular weight forms of the Aβ peptide. Pharmaceutically effective compositions comprising such an antibody or antibodies will be useful in treating and/or preventing beta-amyloid plaque deposition known to be associated with the onset and progression of Alzheimer's disease.

SUMMARY OF THE INVENTION

The present invention relates to an isolated antibody that shows specific binding to a conformational epitope of a protofibril form of β-amyloid peptide. The monomer of wild type beta-amyloid (Aβ) peptide is known in the art and is shown herein as SEQ ID NO: 1. The isolated antibodies of the present invention have affinity for such a repeated conformational epitope for the larger molecular weight protofibril form of the Aβ peptide while showing minimal or no affinity for other forms of Aβ peptide, such as monomer or dimer forms of Aβ peptide.

The present invention also relates to an isolated antibody that specifically interacts with and shows a measurable affinity to a conformational epitope of a protofibril form of Aβ peptide, whereby the protofibril epitope is represented by an exposed region of a Aβ-protofibril form comprising the amino terminal portion of an exposed portion of the Aβ peptide.

The present invention further relates to an isolated antibody that specifically interacts and shows a measurable affinity to a conformational epitope of a protofibril form of Aβ peptide, whereby the protofibril epitope is represented by an exposed region of a Aβ-protofibril form comprising amino acids 1-(SEQ ID NO:2) of an exposed portion of the Aβ peptide.

The present invention also relates to an isolated antibody that specifically interacts and shows a measurable affinity to a conformational epitope of a protofibril form of Aβ peptide, whereby the protofibril epitope is represented by an exposed region of a Aβ-protofibril form which comprises amino acids 4-12 and 9-20 (SEQ ID NOS: 3 and 4, respectively) of an exposed portion of the Aβ peptide.

The present invention relates in part to monoclonal antibodies 13C3, 1D1 and 19A6, and any affinity matured form of 13C3, 1D1 and 19A6. The present invention further relates to an antibody which mimics the functional specificity as described herein for 13C3, 1D1 and 19A6. To this end, the present invention also relates to biologically active fragments and/or mutants of the 13C3, 1D1, 19A6 or a 13C3-, 1D1-, or 19A6-like antibody, including but not necessarily limited to amino acid substitutions (e.g., as a directed form of affinity maturation of the $V_H$ or $V_L$ regions), deletions, additions, amino terminal truncations and carboxy-terminal truncations such that these mutations provide a basis for an antibody or antibody binding portion that results in a similar or improved version of a 13C3, 1D1, 19A6 or 13C3-like antibody binding protein. In one embodiment of this portion of the invention, the $V_H$ and $V_L$ region of 13C3 comprises the amino acid sequence as set forth in SEQ ID NO: 7 ($V_H$) and/or SEQ ID NO:5 ($V_L$), respectively.

The present invention further relates to an isolated nucleic acid molecule comprising a nucleotide sequence which encodes the $V_H$ and/or $V_L$ regions of a 13C3, 1D1 or 19A6 antibody; and especially an isolated nucleic acid molecule (polynucleotide) encoding a biologically relevant portion of 13C3, or affinity matured version or otherwise mutated version of 13C3, 1D1 or 19A6 antibody. To this end, one embodiment of the present invention relates to a nucleic acid molecule which comprises a nucleotide sequence encoding the $V_H$ and $V_L$ region of 13C, as set forth in SEQ ID NO:8 (13C3: $V_H$ region) and SEQ ID NO:6 (13C3: $V_L$ region), respectively.

The present invention also relates to isolated antibodies 13C3, 1D1 or 19A6 as disclosed herein, antibodies that specifically interact and show a measurable affinity to a conformational epitope of a protofibril form of Aβ peptide.

The present invention also relates to a hybridoma capable of producing a monoclonal antibody of the present invention. Particular hybridomas of the present invention include hybridomas which produce exemplified monoclonal antibodies 13C3, 19A6 and 1D1, respectively.

The present invention relates to pharmaceutically effective compositions which comprise an isolated antibody as disclosed and further defined herein: an isolated antibody that specifically interacts with and shows a measured affinity to and ability to specifically bind to a repeating conformational epitope of a protofibril form of Aβ while showing minimal or no measurable affinity to low molecular weight forms of Aβ. These compositions may optionally comprise one or more carriers, one or more excipients, and/or one or more chemical derivatives.

The present invention also relates to methods of treating an individual afflicted with Alzheimer's disease comprising administering to the individual a pharmaceutically effective composition which comprises an isolated antibody disclosed herein, namely an antibody that specifically interacts and shows a measured affinity to a repeating conformational epitope of a protofibril form of Aβ peptide while showing minimal or no detectable affinity toward lower molecular weight forms of Aβ peptide. These methods will provide for a therapeutic intervention so as to reduce the amount of amyloid deposits in the brain of an individual afflicted with Alzheimer's disease. Particular embodiments of this portion of the present invention relate to methods of treating an individual afflicted with Alzheimer's disease comprising administering a pharmaceutically effective composition formulated with an antibody showing specific affinity (as at least compared to low molecular weight forms of Aβ peptide) to a conformational epitope of a protofibril form of Aβ peptide, especially whereby the protofibril epitope is represented by an exposed region of a Aβ-protofibril form which comprises amino acids 1-20 (SEQ ID NO:2) of an exposed portion of the Aβ peptide. Specific embodiments relating to these therapeutic and prophylactic methods disclosed herein may utilize exemplified mouse monoclonal antibodies 13C3, 19A6, 1D1, as well as affinity matured versions of any such antibody, chimeric antibody, humanized antibody, human monoclonal antibody, and/or any other such antibody form known in the art, including but not limited to the antibody or specific binding members reviewed herein. Any such antibody or specific binding member may be referred to within this specification as a "13C3-like antibody." Thus, a "13C3-like antibody" is meant to also encompass the 13C3 monoclonal antibody disclosed herein.

The present invention also relates to methods of screening for and selecting compounds which may act as an inhibitor of fibril and/or senile plaque formation associated with Alzheimer's disease. Such a methodology comprises utilizing an antibody with 13C3-like characteristics (e.g., specific affinity to the PF vs. LMW forms of Aβ peptide) in various antibody/peptide/test compound interaction assays in order to select a compound which modulates the process of fibril and/or plaque formation.

The present invention further relates to diagnostic assay methods to specifically determine protofibril levels within a subject or patient. Such assays may be carried out by any techniques known and available to the artisan, including but not limited to Western blots, ELISAs, radioimmunoassays, immunohistochemical assays, immunoprecipitations, or other immunochemical assays known in the art. Thus, one embodiment of this portion of the invention relates to taking a tissue sample from a subject or patient and determining the level of PF Aβ in the sample using a diagnostic kit and associated assay; whereby the kit comprises a 13C3-like antibody, thus allowing for the specific determination of PF Aβ levels in the tissue sample. The tissue sample for analysis is typically blood, plasma, serum, mucus or cerebral spinal fluid from the subject or patient To this end, the antibodies of the present invention may be utilized for at least the following uses: (1) as a prophylactic or therapeutic agent to prevent or reduce plaque deposits associated with Alzheimer's disease, either alone or in conjunction with any available combination therapy; (2) in designing peptide immunogens that may be used to elicit an effective antibody response in prophylactic or therapeutic vaccination strategies relating to treatment of Alzheimer's disease; (3) to generate a prophylactic or therapeutic anti-idiotypic antibody (Ab2) mimicking the cryptic epitope(s) that bind the antibodies of the present invention; and, (4) in designing peptides derived from the complementarity determining regions (CDRs) of the neutralizing antibodies of the present invention for use in either screening inhibitors of protofibril formation for use in prophylactic and/or therapeutic regimes and (4) as a diagnostic reagent to determine the level of protofibrillar Aβ in serum or CSF of a patient at risk for developing AD.

It is an object of the present invention to provide for antibodies that specifically interact and show affinity to an exposed, conformational epitope of a protofibril form of Aβ peptide which comprises amino acids 1-20 (SEQ ID NO:2) of an exposed portion of the Aβ peptide.

It is a further object of the present invention to provide for antibodies that interact and show affinity to an exposed conformational epitope of a protofibril form of Aβ peptide which comprises amino acids 4-12 and 9-20 (SEQ ID NO:3, 4) of an exposed portion of the Aβ peptide.

Another object of the present invention is to provide 13C3-like antibodies which prevent or reduce Aβ peptide protofibril formation linked to the deposition of plaques associated with Alzheimer's disease.

Another object of the present invention is to provide assays utilizing 13C3-like antibodies in antibody/peptide/test compound interaction assays to select compounds which will be useful in treating plaque deposition associated with Alzheimer's disease.

As used herein, "Ka" is intended to refer to the association constant of a particular antibody antigen interaction, "Kd" is intended to refer to the dissociation constant of a particular antibody-antigen interaction.

As used herein, the term "epitope" or "antigenic determinant" refers to a site on an antigen to which B and/or T cells respond or a site on a molecule against which an antibody will be produced and/or to which an antibody will bind. For example, an epitope can be recognized by an antibody defining the epitope. An epitope can be either a "linear epitope" (where a primary amino acid primary sequence comprises the epitope; typically at least 3 contiguous amino acid residues, and more usually, at least 5, and up to about 8 to about 10 amino acids in a unique sequence) or a "conformational epitope" (an epitope wherein the primary, contiguous amino acid sequence is not the sole defining component of the epitope). A conformational epitope may comprise an increased number of amino acids relative to a linear epitope, as this conformational epitope recognizes a three-dimensional structure of the peptide or protein. For example, when a protein molecule folds to form a three dimensional structure, certain amino acids and/or the polypeptide backbone forming the conformational epitope become juxtaposed enabling the antibody to recognize the epitope. Methods of determining conformation of epitopes include but are not limited to, for example, x-ray crystallography, two-dimensional nuclear magnetic resonance spectroscopy and site-directed spin labeling and electron paramagnetic resonance spectroscopy. See, for example, *Epitope Mapping Protocols in Methods in Molecular Biology*, Vol. 66, Glenn E. Morris, Ed. (1996), the disclosure of which is incorporated in its entirety herein by reference.

As used herein, "specific binding" between two entities means an affinity of at least $10^6$ $M^{-1}$, $10^7$ $M^{-1}$, $10^8$ $M^{-1}$, $10^8 M^{-1}$, or $10^{10}$ $M^{-1}$.

As used herein, "protofibrils" are protofibrillar aggregates which include spherical structures comprising Aβ peptides that appear to represent strings of the spherical structures forming curvilinear structures.

As used herein, the term "isolated" is used herein as it is used within the art. Namely, the state in which antibodies/specific binding members, nucleic acid molecules and the such are found. Antibodies/specific binding members and nucleic acid molecules will be free or substantially free of material with which they are naturally associated such as other polypeptides or nucleic acids with which they are found in their natural environment, or the environment in which they are prepared (e.g. cell culture) when such preparation is by recombinant DNA technology (practiced ill vitro) or in vivo. "Isolated" covers any form containing the identified and characterized component(s) of the present invention following removal from that initial environment. Examples, but certainly not limitations, include pharmaceutical formulations, formulation with diluents, antibodies/specific binding members, nucleic acid molecules and portions thereof which have been modified (e.g., antibody glycosylation) either in vitro or in vivo and removed from that environment.

As used herein, the term "recombinant human antibody" represents a viable subset of "antibodies" generated by various means of recombinant DNA technology and non-human transgenics that are well known in the art. Such methodology is utilized to generate an antibody from one or the following origins: (i) a scFv or alternative antibody isolated from a combinatorial human antibody library; (ii) a partial or complete antibody generated from a respective expression vector stably or transiently transfected into a host cell, preferably a mammalian host cell (e.g., subcloning nucleotide sequences encoding VH and VL chains into an expression vector in conjunction with respective CH and CL nucleotide sequences, so as to promote expression of a predetermined form of antibody showing specificity to the PF form of Aβ); and/or (iii) an antibody isolated from a non-human transgenic animal which contains human immunoglobulin genes, or by any other known methodology which relies of the recombinant 'mixing and matching' of human immunoglobulin gene sequences to other DNA sequences in order to generate the human recombinant antibody of interest.

The terms "subject" or "patient" is meant to include any member of the Phylum Chordata, including, without limitation, humans and other primates, including nonhuman primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like.

The term "treating" or "treatment" of a disease refers to executing a protocol, which may include administering one or more drugs to a subject (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In the case of Alzheimer's disease, "preventing" or "preventing" may also occur in a situation where a course of treatment is advanced in order to prevent or stall onset of the symptoms associated with Alzheimer's disease. In addition, "treating" or "treatment" does not require complete alleviation of signs or symptoms, does not require a cure, and specifically includes protocols which have only a marginal positive effect on the subject.

As used herein, the term "active ingredient" refers to a 13C3-like antibody which shows affinity and specificity (e.g., specific binding) to the amino terminal portion of the protofibril structure of beta-amyloid.

As used herein, the terms "effective amount" or "pharmaceutically effective amount" of antibody, as provided herein, refers to a nontoxic but sufficient amount of the active ingredient in order to provide the desired biological result. An appropriate "effective" amount in any individual case may be determined by one of ordinary skill in the art using routine experimentation.

As used herein, the terms "pharmaceutically acceptable" or "pharmacologically acceptable" mean a material may be administered to an individual in a drug delivery device along with the formulated biological agent without causing any undesirable biological effects or interacting in a deleterious manner with any of the components of the composition in which it is contained (e.g., a "pharmaceutically acceptable composition").

As used herein, the phrases "physiologically acceptable carrier" and "pharmaceutically acceptable carrier" which may be interchangeably used refer to a carrier, diluent, and excipient that does not cause significant irritation to an organism and does not abrogate the biological activity and properties of the administered compound. An adjuvant is included under these phrases.

As used herein, the term "excipient" refers to an inert substance added to a pharmaceutical composition to further facilitate administration of an active ingredient.

The term "minimal affinity" as used in comparing affinity of the antibodies for the protofibrillar form of the Aβ peptide with affinity of the antibodies for other forms of Aβ peptide, such as fibrils, sheet structures, and low molecular weight oligomers and monomers, indicates that ratio of the affinity for the protofibrillar Aβ form to the affinity for other Aβ forms is greater than about 2. Preferably, the ratio is greater than about 3, or about 4, or about 5.

BRIEF DESCRIPTION OF THE FIGURES

FIG. 5A illustrates a Western Dot Blot analysis with monoclonal antibodies 13C3 (top panel), 1D1 (middle panel) and 4G8 (bottom panel) against a series of overlapping 13 amino acid peptides as described in Example 5. FIG. 5B illustrates amino acid sequence of Aβ1-42 (SEQ ID NO:1), as well as the predicted epitopes of monoclonal antibodies 13C3, and 1D1.

FIG. 10 shows the nucleotide and amino acid sequences of the cloned light chain variable region (SEQ ID Nos: 5 and 6) and heavy chain variable region (SEQ ID NOs: 7 and 8) for mAb 13C3.

DETAILED DESCRIPTION OF THE INVENTION

Figure 1:
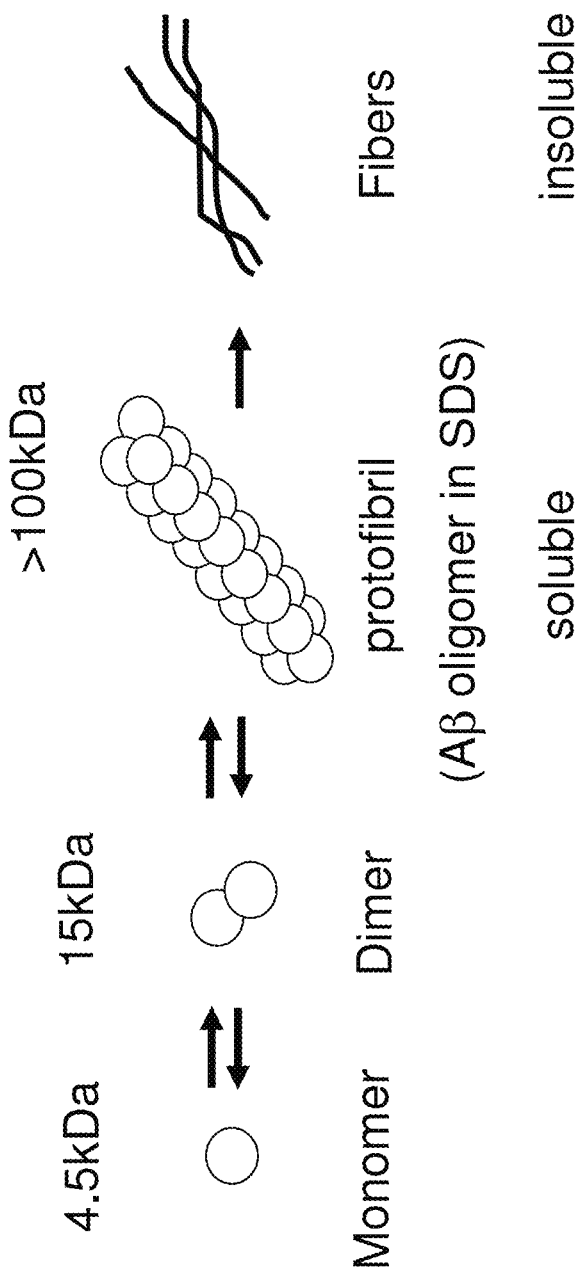
FIG. 1 shows the process of Aβ fibrillogenesis, including formation of protofibril oligomers.

The amyloid precursor protein (APP) plays an important role in the pathogenesis of Alzheimer's disease (AD). Proteolytic processing of APP by β- and γ-secretases generate Aβ peptides (Aβ) which normally range in the length from 39 to 43 amino acids in length. The onset of Alzheimer's disease is characterized by the accumulation of oligmeric or aggregated forms of Aβ in the brain. The immunological compositions of the present invention are useful in treating or preventing Alzheimer's disease, for use as reagents in diagnostic assays, as well as for designing small molecule inhibitors of amyloid deposition. The 13C3-like antibodies of the present invention may be administered prophylactically to the general population of a mammal, especially a human, in a contemplated pharmaceutically acceptable formulation in an amount and/or dosage regime sufficient to eliminate, reduce or delay onset of the disease. Methods of prophylactic treatment are especially warranted with individuals known to be at a genetic or familiar risk of Alzheimer's disease. Numerous genetic markers of risk for Alzheimer's disease have been identified, including but not limited to APP mutations (e.g., the Indian mutation (Val717Phe), the Swedish mutations (Lys670Asn, Met671Leu), the Hendricks mutation (Ala692Gly), the Dutch mutation (Glu693Gln), the Iranian mutation (Thr714Ala), the German mutation (Val715Ala), and the Florida mutation (Ile716Val), to list a few. Additional mutations which may indicate an increased risk of Alzheimer's disease include mutations in the presenilin genes (PS1 and PS2) and ApoE4. The present invention also relates to therapeutic intervention via pharmaceutically acceptable compositions comprising a 13C3-like antibody for individuals presently suffering from Alzheimer's disease can be recognized from characteristic dementia, especially in the presence of risk factors described above or already suffering from such a disease in an amount sufficient to cure, or at least partially arrest, the Alzheimer's disease symptoms and complications. Either prophylactic- or therapeutic-based treatment methods contemplated herein may be used to address early or late onset Alzheimer's disease. In view of the importance of oligomeric forms of Aβ in the onset of Alzheimer's disease, the present invention relates to an isolated antibody that specifically interacts and shows a measured affinity to a repeating conformational epitope of a protofibril form of Aβ peptide. The monomer of wild type Aβ peptide ($Aβ_{42}$; the 42 amino acid form) is known in the art and is shown herein as SEQ ID NO:1:

Asp Ala Glu Phe Arg His Asp Ser Gly Tyr Glu Val His His Gln Lys Leu Val Phe Phe Ala Glu Asp Val Gly Ser Asn Lys Gly Ala Ile Ile Gly Leu Met Val Gly Gly Val Val Ile Ala (SEQ ID NO:1).

The isolated antibodies of the present invention will show affinity for a repeated conformational epitope of the larger molecular weight, oligomeric protofibrillar form of the Aβ peptide while showing minimal affinity for other forms of Aβ peptide, such as low molecular weight monomers and dimers.

The present invention also relates to an isolated antibody that interacts and shows a measurable affinity to a conformational epitope of a protofibril form of Aβ peptide, whereby the protofibril epitope is represented by an exposed region of a Aβ-protofibril form which comprises the amino terminal portion of an exposed portion of the Aβ peptide.

The present invention further relates to an isolated antibody that specifically interacts and shows a measurable affinity to a conformational epitope of a protofibril form of Aβ peptide, whereby the protofibril epitope is represented by an exposed region of a Aβ-protofibril form which comprises amino acids 1-20 (SEQ ID NO:2) of an exposed portion of the Aβ peptide, as follows: Asp Ala Glu Phe Arg His Asp Ser Gly Tyr Glu Val His His Gln Lys Leu Val Phe Phe (SEQ ID NO:2).

As exemplified herein, mouse monoclonal antibodies have been identified which specifically show specific affinity for the protofibril (PF) form of the Aβ peptide, while showing minimal affinity for low molecular weight species of the Aβ peptide. The dimer form of Aβ (~15 kDa) over time polymerizes to form a soluble PF form of Aβ, with a molecular weight of approximately 670 kDa. Mice were immunized with this higher molecular weight PF Aβ. Monoclonal antibodies were screened for specificity to the high molecular weight PF form of the Aβ peptide while showing minimal or no ability to bind lower molecular weight forms of Aβ. This portion of the present invention is exemplified by the screening, isolation and characterization of the 13C3 series of monoclonal antibodies raised against the ~670 kDa high molecular weight protofibril form of the Aβ peptide (i.e., 13C3, 1D1 and 19A6). This series of monoclonal antibodies shows the intended specificity in vitro while also reducing Alzheimer's disease-associated plaque formation in a transgenic mouse Alzheimer's disease model. Thus, in a particular embodiment of the invention, the isolated antibody specifically interacts and shows a measurable affinity to a conformational epitope of a protofibril form of Aβ peptide, whereby the protofibril epitope is represented by an exposed region of a Aβ-protofibril form which comprises amino acids 4-12 (SEQ ID NO:3) and 9-20 (SEQ ID NO:4) of an exposed portion of the Aβ peptide: Phe Arg His Asp Ser Gly Tyr Glu Val (SEQ ID NO:3); Gly Tyr Glu Val His His Gln Lys Leu Val Phe Phe (SEX ID NO:4).

One embodiment of the present invention relates to an antibody which comprises a $V_H$ (SEQ ID NO: 7) and/or $V_L$ (SEQ ID NO: 5) region as disclosed for 13C3, so as to impart 13C3-like specificity to the PF versus LMW form of the Aβ peptide. An additional embodiment is a 13C3-like antibody or biologically relevant fragment thereof which show specificity to the PF form over the LMW form of the Aβ peptide. Thus, the present invention also relates to biologically active fragments and/or mutants of the 13C3, 1D1, 19A6 or a 13C3-like antibody, including but not necessarily limited to amino acid substitutions (e.g., as a directed form of affinity maturation of the $V_H$ or $V_L$ regions), deletions, additions, amino terminal truncations and carboxy-terminal truncations such that these mutations provide a basis for an antibody or antibody binding portion that results in a similar or improved version of a 13C3, 1D1, 19A6 or 13C3-like antibody binding protein. As noted herein, one embodiment of this portion of the invention related to the $V_H$ and/or $V_L$ region of such an antibody comprising the amino acid sequence as set forth in SEQ ID NO: 7 and/or SEQ ID NO:5, respectively. The present invention notes the existence of codon redundancy which may result in differing DNA molecules expressing an identical antibody or portion thereof (e.g., alternative nucleic acid molecules encoding an identical scFv or a VH and/or VL portion of an IgG). For purposes of this specification, a sequence bearing one or more replaced codons will be defined as a degenerate variation. Another source of sequence variation may occur through RNA editing. Such RNA editing may result in another form of codon redundancy, wherein a change in the open reading frame does not result in an altered amino acid residue in the expressed protein. Also included within the scope of this invention are mutations either in the DNA sequence or the translated antibody which improve the ultimate physical properties of the expressed antibody. To this end, the present invention relates to (i) affinity matured versions of a 13C3, 1D1, 19A6 or any other such 13C3-like antibody, and/or (ii) mutated forms of 13C3, 1D1, 19A6 or any other such 13C3-like antibody, including but not limited to one or more mutations in the CDR1, CDR2 an/or CDR3 regions as generated through known affinity maturation methodology and recombinant DNA techniques known for introducing site specific mutations. Thus, the isolated antibodies of the present invention are antibodies that specifically interact with a conformational epitope of a protofibril form of Aβ peptide. The isolated antibodies of the present invention will show affinity for such a conformational epitope for the larger molecular weight protofibrillar form of the Aβ peptide while showing minimal affinity for other forms of Aβ peptide, such as fibrils, sheet structures, and low molecular weight oligomers and monomers.

The present invention also relates to the isolated monoclonal antibody, 13C3. This portion of the invention also relates to a hybridoma which produces the monoclonal antibody, 13C3. A hybridoma which produces the monoclonal antibody 13C3 is available under ATCC Accession No. PTA-8830. This hybridoma was deposited on Dec. 5, 2007 with the American Type Culture Collection, 10801 University Boulevard, Manassas, Va. 20110-2209, USA and was given the deposit number PTA-8830.

The present invention also relates to the isolated monoclonal antibody, 1D1. This portion of the invention also relates to a hybridoma which produces the monoclonal antibody, 1D1.

The present invention also relates to the isolated monoclonal antibody, 19A6. This portion of the invention also relates to a hybridoma which produces the monoclonal antibody, 19A6.

The present invention also relates to methods of screening for and selecting compounds which may act as an inhibitor of fibril and/or senile plaque formation associated with Alzheimer's disease. Such methodology comprises utilizing an antibody with 13C3-like affinity to the PF form of Aβ peptide in various antibody/peptide/test compound interaction assays in order to select a compound which modulates the process of fibril and/or plaque formation. The compound may be a non-proteinaceous organic or inorganic molecule, a peptide (e.g., as a potential prophylactic or therapeutic peptide vaccine), a protein, DNA (single or double stranded) or RNA (such as siRNA or shRNA). It will become evident upon review of the disclosure and teachings of this specification that any such peptide or small molecule which effectively competes with a 13C3-like antibody for binding to the PF form of Aβ peptide represents a possible lead compound relating to prophylactic or therapeutic treatment of Alzheimer's disease. To this end, interaction assays may be utilized for the purpose of high throughput screening to identify compounds that occupy or interact with the 13C3 epitopes of the PF form of Aβ peptide and displace the antibody.

Various antibody/antigen-based assays known in the art may be used which incorporate and rely on a 13C3-like antibody of the present invention as an essential reagent in screening for compounds useful in the prophylactic or therapeutic treatment of Alzheimer's disease (e.g., a small inorganic molecule or candidate peptide vaccine), including but not limited to an ELISA assay, a radioimmune assay, a Western blot analysis, any homogenous assay relying on a detectable biological interaction not requiring separation or wash steps (e.g., see AlphaScreen from PerkinElmer) and/or SPR-based technology (e.g., see BIACore)). Compounds and/or peptide vaccine candidates identified through use of a 13C3-like antibody may be detected by a variety of assays. The assay may be a simple "yes/no" assay to determine whether there is a change in the ability to form the known antibody/antigen complex, or may be made quantitative in nature by utilizing an assay such as an ELISA based assay, a homogenous assay, or an SPR-based assay. To this end, the present invention relates to any such assay, regardless of the known methodology employed, which measures the ability of a test compound to compete with 13C3-like antibody, to an appropriate peptide or protein mimetic of the amino terminal portion of a 13C3 epitope of the PF form of Aβ peptide.

The antibodies described herein may be used as the basic reagents in a number of different immunoassays to determine the presence of a Aβ protofibril form in a tissue sample. Generally speaking, the antibodies can be employed in any type of immunoassay, whether qualitative or quantitative. This includes both the two-site sandwich assay and the single site immunoassay of the non-competitive type, as well as in traditional competitive binding assays. One embodiment of interest, for ease of detection, and its quantitative nature, is the sandwich or double antibody assay, of which a number of variations exist, all of which are intended to be encompassed by this portion of the present invention. For example, in a typical forward sandwich assay, unlabeled antibody is immobilized on a solid substrate, e.g., microtiter plate wells, and the sample to be tested is brought into contact with the bound molecule. After a suitable period of incubation, for a period of time sufficient to allow formation of an antibody-antigen binary complex, a second antibody, labeled with a reporter molecule capable of inducing a detectable signal, is then added and incubation is continued allowing sufficient time for binding with the antigen at a different site and the formation of a ternary complex of antibody-antigen-labeled antibody. Any unreacted material is washed away, and the presence of the antigen is determined by observation of a signal, which may be quantitated by comparison with a control sample containing known amounts of antigen. Variations on the forward sandwich assay include the simultaneous assay, in which both sample and antibody are added simultaneously to the bound antibody, or a reverse sandwich assay in which the labeled antibody and sample to be tested are first combined, incubated and added to the unlabelled surface bound antibody. These techniques are well known to those skilled in the art, and the possibility of minor variations will be readily apparent. As used herein, "sandwich assay" is intended to encompass all variations on the basic two-site technique.

For the sandwich assays of the present invention, the only limiting factor is that both antibodies have different binding specificities for the Aβ protofibril form. Thus, a number of possible combinations are possible. As a more specific example, in a typical forward sandwich assay, a primary antibody is either covalently or passively bound to a solid support. The solid surface is usually glass or a polymer, the most commonly used polymers being cellulose, polyacrylamide, nylon, polystyrene, polyvinylchloride or polypropylene. The solid supports may be in the form of tubes, beads, discs or microplates, or any other surfaces suitable for conducting an immunoassay. The binding processes are well known in the art. Following binding, the solid phase-antibody complex is washed in preparation for the test sample. An aliquot of the body fluid containing a Aβ protofibril form to be tested is then added to the solid phase complex and incubated at 25° C. for a period of time sufficient to allow binding of any Aβ protofibril form protein present to the antibody specific for the Aβ protofibril form. The second antibody is then added to the solid phase complex and incubated at 25° C. for an additional period of time sufficient to allow the second antibody to bind to the primary antibody-antigen solid phase complex. The second antibody is linked to a reporter molecule, the visible signal of which is used to indicate the binding of the second antibody to any antigen in the sample. By "reporter molecule", as used in the present specification is meant a molecule which by its chemical nature, provides an analytically detectable signal which allows the detection of antigen-bound antibody. Detection must be at least relatively quantifiable, to allow determination of the amount of antigen in the sample, this may be calculated in absolute terms, or may be done in comparison with a standard (or series of standards) containing a known normal level of antigen.

The most commonly used reporter molecules in this type of assay are either enzymes or fluorophores. In the case of an enzyme immunoassay an enzyme is conjugated to the second antibody, often by means of glutaraldehyde or periodate. As will be readily recognized, however, a wide variety of different conjugation techniques exist, which are well known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. In all cases, the enzyme-labeled antibody is added to the first antibody-Aβ protofibril protein complex and allowed to bind to the complex, and then the excess reagent is washed away. A solution containing the appropriate substrate is then added to the tertiary complex of antibody-antigen-labeled antibody. The substrate reacts with the enzyme linked to the second antibody, giving a qualitative visual signal, which may be further quantitated, usually spectrophotometrically, to give an evaluation of the amount of antigen that is present in the serum sample.

Additionally, fluorescent compounds, such as fluorescein or rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. As in the enzyme immunoassay (EIA), the fluorescent-labelled antibody is allowed to bind to the first antibody-Aβ protofibril form protein complex. After washing the unbound reagent, the remaining ternary complex is then exposed to light of the appropriate wavelength, and the fluorescence observed indicates the presence of the antigen. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

In another embodiment, the sample to be tested (e.g., human blood or spinal fluid containing a Aβ protofibril form) may be used in a single site immunoassay wherein it is adhered to a solid substrate either covalently or noncovalently. An unlabeled anti-Aβ protofibril protein antibody is brought into contact with the sample bound on the solid substrate. After a suitable period of incubation, for a period of time sufficient to allow formation of an antibody-antigen binary complex a second antibody, labelled with a reporter molecule capable of inducing a detectable signal, is then added and incubation is continued allowing sufficient time for the formation of a ternary complex of antigen-antibody-labeled antibody. For the single site immunassay, the second antibody may be a general antibody (i.e., zenogeneic antibody to immunoglobulin, particularly anti-(IgM and IgG) linked to a reporter molecule) that is capable of binding an antibody that is specific for the Aβ protofibril protein form of interest.

A 13C3-like antibody may take one of numerous forms known in the art. Antibodies may take the form of any type of relevant antibody fragment, antibody binding portion, specific binding member, a non-protein synthetic mimic, or any other relevant terminology known in the art which refers to an entity which at least substantially retains the binding specificity/neutralization activity. Thus, the term "antibody" as used in any context within this specification is meant to include, but not be limited to, any specific binding member, immunoglobulin class and/or isotype (e.g., $IgG_1$, $IgG_2$, $IgG_3$, $IgG_4$, IgM, IgA, IgD, IgE and IgM); and biologically relevant fragment or specific binding member thereof, including but not limited to Fab, F(ab')2, Fv, and scFv (single chain or related entity). Therefore, it is well known in the art, and is included as review only, that an "antibody" refers to a glycoprotein comprising at least two heavy (H) chains and two light (L) chains inter-connected by disulfide bonds, or an antigen binding portion thereof. A heavy chain is comprised of a heavy chain variable region (VH) and a heavy chain constant region (CH1, CH2 and CH3). A light chain is comprised of a light chain variable region (VL) and a light chain constant region (CL). The variable regions of both the heavy and light chains comprise framework regions (FWR) and complementarity determining regions (CDR). The four FWR regions are relatively conversed while CDR regions (CDR1, CDR2 and CDR3) represent hypervariable regions and are arranged from $NH_2$ terminus to the COOH terminus as follows: FWR1, CDR1, FWR2, CDR2, FWR3, CDR3, FWR4. The variable regions of the heavy and light chains contain a binding domain that interacts with an antigen while, depending of the isotype, the constant region(s) may mediate the binding of the immunoglobulin to host tissues or factors. That said, also included in the working definition of "antibody" are chimeric antibodies, humanized antibodies, a recombinant antibody, as human antibodies generated from a transgenic non-human animal, as well as antibodies selected from libraries using enrichment technologies available to the artisan. Antibody fragments are obtained using techniques readily known and available to those of ordinary skill in the art, as reviewed below. Therefore, an "antibody" is any such entity or specific binding member, which specifically binds the conformational epitope of the protofibril form of Aβ as described herein. Therefore, the term "antibody" describes an immunoglobulin, whether natural or partly or wholly synthetically produced; any polypeptide or protein having a binding domain which is, or is substantially homologous to, an antibody binding domain. These can be derived from natural sources, or they may be partly or wholly synthetically produced. Examples of antibodies are the immunoglobulin isotypes and their isotypic subclasses; fragments which comprise an antigen binding domain such as Fab, scFv, Fv, dAb, Fd and diabodies, as discussed without limitation, infra. It is known in the art that it is possible to manipulate monoclonal and other antibodies and use techniques of recombinant DNA technology to produce other antibodies or chimeric molecules which retain the specificity of the original antibody Such techniques may evolve introducing DNA encoding the immunoglobulin variable region, or the complementarity determining regions (CDRs), of an antibody to the constant regions, or constant regions plus framework regions, of a different immunoglobulin. A hybridoma or other cell producing an antibody may be subject to genetic mutation or other changes, which may or may not alter the binding specificity of antibodies produced. Antibodies can be modified in a number of ways, and the term "antibody" should be construed as covering any specific binding member or substance having a binding domain with the required specificity. Thus, this term covers antibody fragments, derivatives, functional equivalents and homologues of "antibody" including any polypeptide comprising an immunoglobulin binding domain, whether natural or wholly or partially synthetic. Such an entity may be a binding fragment encompassed within the term "antigen-binding portion" or "specific binding member" of an antibody including but not limited to (i) a Fab fragment, a monovalent fragment consisting of the VL, VH, CL and CH domains; (ii) a F(ab')2 fragment, a bivalent fragment comprising two Fab fragments linked by a disulfide bridge at the hinge region; (iii) a Fd fragment consisting of the VH and CH domains; (iv) a Fv fragment consisting of the VL and VH domains of a single arm of an antibody (v) a dAb fragment, which comprises a VH domain; (vi) an isolated complementarity determining region (CDR); (vii) a 'scAb', an antibody fragment containing VH and VL as well as either CL or CH; and (viii) artificial antibodies based upon protein scaffolds, including but not limited to fibronectin type III polypeptide antibodies (e.g., see U.S. Pat. No. 6,703,199, issued to Koide on Mar. 9, 2004 and PCT International Application Publication No. WO 02/32925). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)).

In one embodiment, the variable light (VL) region for the isolated 13C3 or 13C3-like antibodies of the present invention may comprise a 113 amino acid peptide sequence (SEQ ID NO: 5) which is encoded by a 339 base pair nucleotide sequence (SEQ ID NO: 6):

```
                                                        (SEQ ID NO: 5)
Asp Val Val Met Thr Gln Thr Pro Leu Ser Leu Pro Val Ser Leu Gly

Asp Gln Ala Ser Ile Ser Cys Arg Ser Gly Gln Ser Leu Val His Ser

Asn Gly Asn Thr Tyr Leu His Trp Tyr Leu Gln Lys Pro Gly Gln Ser

Pro Lys Leu Leu Ile Tyr Thr Val Ser Asn Arg Phe Ser Gly Val Pro

Asp Arg Phe Ser Gly Ser Gly Ser Gly Ser Asp Phe Thr Leu Lys Ile
```

-continued

Ser Arg Val Glu Ala Glu Asp Leu Gly Val Tyr Phe Cys Ser Gln Asn

Thr Phe Val Pro Trp Thr Phe Gly Gly Gly Thr Lys Leu Glu Ile Lys

Arg (SEQ ID NO: 6)
GATGTTGTGATGACCCAAACTCCACTCTCCCTGCCTGTCAGTCTTGGAGATCAAGCCTCCATCT

CTTGCAGATCTGGTCAGAGCCTTGTACACAGTAATGGAAACACCTATTTACATTGGTACCTGCA

GAAGCCAGGCCAGTCTCCAAAGCTCCTGATCTATACAGTTTCCAACCGATTTTCTGGGGTCCCG

GACAGGTTCAGTGGCAGTGGATCAGGGTCAGATTTCACACTCAAGATCAGCAGAGTGGAGGCTG

AGGATCTGGGAGTTTATTTCTGCTCTCAAAATACATTTGTTCCTTGGACGTTCGGTGGAGGCAC

CAAGCTGGAAATCAAACGG

In a further embodiment, the variable heavy (VH) region for the isolated 13C3 or 13C3-like antibodies of the present invention may comprise a 115 amino acid peptide sequence (SEQ ID NO: 7) encoded by a 345 base pair nucleotide sequence (SEQ ID NO: 8):

(SEQ ID NO: 7)
Gln Val Gln Leu Gln Gln Ser Gly Pro Glu Leu Val Arg Pro Gly Val

Ser Val Lys Ile Ser Cys Lys Gly Ser Gly Tyr Thr Phe Thr Asp Tyr

Ala Met His Trp Val Lys Gln Ser His Ala Lys Ser Leu Glu Trp Ile

Gly Val Ile Ser Thr Lys Tyr Gly Lys Thr Asn Tyr Asn Gln Lys Phe

Lys Gly Lys Ala Thr Met Thr Val Asp Lys Ser Ser Ser Thr Ala Tyr

Met Glu Leu Ala Arg Leu Thr Ser Glu Asp Ser Ala Ile Tyr Tyr Cys

Ala Arg Gly Asp Asp Gly Tyr Ser Trp Gly Gln Gly Thr Ser Val Thr

Val Ser Ser;

(SEQ ID NO: 8)
CAGGTCCAGCTGCAGCAGTCTGGGCCTGAGCTGGTGAGGCCTGGGGTCTCAGTGAAGATTTCCT

GCAAGGGTTCCGGCTACACATTCACTGATTATGCTATGCACTGGGTGAAGCAGAGTCATGCAAA

GAGTCTAGAGTGGATTGGAGTTATTAGTACTAAGTATGGTAAGACAAACTACAACCAGAAGTTT

AAGGGCAAGGCCACAATGACTGTTGACAAATCCTCCAGCACAGCCTATATGGAGCTTGCCAGAT

TGACATCTGAGGATTCTGCCATCTATTACTGTGCAAGAGGGGACGATGGTTATTCCTGGGGTCA

AGGAACCTCAGTCACCGTCTCCTCA.

In a further embodiment, the framework regions, FWR1, FWR2, FWR3, and FWR4, of the VL chain may be comprised of amino acid set forth in SEQ ID NO:9, SEQ ID NO:10, SEQ ID NO:11, and SEQ ID NO:12, respectively, as follows:

(SEQ ID NO: 9)
Asp Val Val Met Thr Gln Thr Pro Leu Ser Leu Pro Val Ser Leu Gly

Asp Gln Ala Ser Ile Ser Cys Arg Ser Gly;

(SEQ ID NO: 10)
Leu His Trp Tyr Leu Gln Lys Pro Gly Gln Ser Pro Lys Leu Leu Ile

Tyr;

(SEQ ID NO: 11)
Asn Arg Phe Ser Gly Val Pro Asp Arg Phe Ser Gly Ser Gly Ser Gly

Ser Asp Phe Thr Leu Lys Ile Ser Arg Val Glu Ala Glu Asp Leu Gly

```
Val Tyr Phe Cys;

(SEQ ID NO: 12)
Phe Gly Gly Gly Thr Lys Leu Glu Ile Lys Arg.
```

In a further embodiment, the complementarity determining regions, CDR1, CDR2, and CDR3, of the VL chain may be comprised of the amino acids set forth in SEQ ID NO: 13, SEQ ID NO: 14, SEQ ID NO: 15, respectively, as follows:

```
                                                          (SEQ ID NO: 13)
Gln Ser Leu Val His Ser Asn Gly Asn Thr Tyr;

(SEQ ID NO: 14)
Thr Val Ser;

(SEQ ID NO: 15)
Ser Gln Asn Thr Phe Val Pro Trp Thr.
```

In a further embodiment, the framework regions, FWR1, FWR2, FWR3, and FWR4, of the VH chain may be comprised of the amino acids set forth in SEQ ID NO: 16, SEQ ID NO: 17, SEQ ID NO: 18, and SEQ ID NO: 19, respectively, as follows:

```
                                                          (SEQ ID NO: 16)
Gln Val Gln Leu Gln Gln Ser Gly Pro Glu Leu Val Arg Pro Gly Val

Ser Val Lys Ile Ser Cys Lys;

(SEQ ID NO: 17)
Met His Trp Val Lys Gln Ser His Ala Lys Ser Leu Glu Trp Ile Gly

Val;

(SEQ ID NO: 18)
Ala Thr Met Thr Val Asp Lys Ser Ser Ser Thr Ala Tyr Met Glu Leu

Ala Arg Leu Thr Ser Glu Asp Ser Ala Ile Tyr Tyr Cys Ala Arg;

(SEQ ID NO: 19)
Trp Gly Gln Gly Thr Ser Val Thr Val Ser Ser.
```

In a further embodiment, the complementarity determining regions, CDR1, CDR2, and CDR3, of the VH chain may be comprised of the amino acids set forth in SEQ ID NO: 20, SEQ ID NO: 21, SEQ ID NO: 22, respectively, as follows:

```
                                                          (SEQ ID NO: 20)
Gly Ser Gly Tyr Thr Phe Thr Asp Tyr Ala;

(SEQ ID NO: 21)
Ile Ser Thr Lys Tyr Gly Lys Thr Asn Tyr Asn Gln Lys Phe Lys Gly

Lys;

(SEQ ID NO: 22)
Gly Asp Asp Gly Tyr Ser.
```

Polyclonal or monoclonal antibodies for use in the disclosed treatment methods may be raised by known techniques. Monospecific murine (mouse) antibodies showing specificity to a conformational epitope of a target of choice may be purified from mammalian antisera containing antibodies reactive against this region, or may be prepared as monoclonal antibodies using the technique of Kohler and Milstein (1975, Nature 256: 495-497). Monospecific antibody as used herein is defined as a single antibody species or multiple antibody species with homogenous binding characteristics, such as the mouse monoclonal antibodies exemplified herein with the 13C3 series of monoclonal antibodies. Hybridoma cells are produced by mixing the splenic lymphocytes with an appropriate fusion partner, preferably myeloma cells, under conditions which will allow the formation of stable hybridomas. The splenic antibody producing cells and myeloma cells are fused, selected, and screened for antibody production. Hybridoma cells from antibody positive wells are cloned by a technique such as the soft agar technique of MacPherson (1973, Soft Agar Techniques, in *Tissue Culture Methods and Applications*, Kruse and Paterson, Eds, Academic Press). Monoclonal antibodies are produced in vivo by injecting respective hydridoma cells into pristine primed mice, collecting ascite fluid after an interval of time, and prepared by techniques well known in the art.

Beyond species specific monoclonal antibodies described above, the antibodies of the present invention may also be in the form of a "chimeric antibody", a monoclonal antibody constructed from the variable regions derived from say, the murine source, and constant regions derived from the intended host source (e.g., human; for a review, see Morrison and Oi, 1989, *Advances in Immunology*, 44: 65-92). For example, the variable light and heavy DNA sequences (e.g. SEQ ID NO: 6 and 8, respectively) from the rodent (e.g., mouse) antibody may be cloned into a mammalian expression vector. These light and heavy "chimeric" expression vectors are cotransfected into a recipient cell line and selected and expanded by known techniques. This cell line may then be subjected to known cell culture techniques, resulting in production of both the light chain and heavy chain of a chimeric antibody. Such chimeric antibodies have historically been shown to have the antigen-binding capacity of the original rodent monoclonal while significantly reducing immunogenicity problems upon host administration.

A logical improvement to the chimeric antibody is the "humanized antibody," which arguably reduces the chance of the patient mounting an immune response against a therapeutic antibody when compared to use of a chimeric or full murine monoclonal antibody The strategy of "humanizing" a murine Mab is based on replacing amino acid residues which differ from those in the human sequences by site directed mutagenesis of individual residues or by grafting of entire complementarity determining regions (Jones et al., 1986, Nature 321: 522-526). This technology is again now well known in the art and is represented by numerous strategies to improve on this technology; namely by implementing strategies including, but not limited to, "reshaping" (see Verhoeyen, et al., 1988, *Science* 239: 1534-1536), "hyperchimerization" (see Queen, et al., 1991, *Proc. Natl. Acad. Sci.* 88:2869-2873) or "veneering" (Mark, et al., 1994, Derivation of Therapeutically Active Humanized and Veneered anti-CD18 Antibodies Metcalf end Dalton, eds. *Cellular Adhesion: Molecular Definition to Therapeutic Potential*. New York: Plenum Press, 291-312). These strategies all involve to some degree sequence comparison between rodent and human sequences to determine whether specific amino acid substitutions from a rodent to human consensus is appropriate. Whatever the variations, the central theme involved in generating a humanized antibody relies on CDR grafting, where these three antigen binding sites from both the light and heavy chain are effectively removed from the rodent expressing antibody clone and subcloned (or "grafted") into an expression vector coding for the framework region of the human antibody. For example, utilizing the above techniques a humanized antibody may be expressed wherein the CDR1, CDR2, and CDR3 regions of the variable light chain are set forth in SEQ ID NOS: 13, 14 and 15, respectively, and the CDR1, CDR2, and CDR3 regions of the variable heavy chain are set forth in SEQ ID NOS 20, 21 and 22, respectively. Therefore, a "humanized antibody" is effectively an antibody constructed with only murine CDRs (minus any additional improvements generated by incorporating one or more of the above mentioned strategies), with the remainder of the variable region and all of the constant region being derived from a human source.

The present invention also relates to isolated nucleic acid molecules and associated amino acid sequences which relate to the $V_H$ and/or $V_L$ regions of the 13C3 antibody, and more specifically, an isolated nucleic acid molecule (polynucleotide) encoding a biologically relevant portion of 13C3, or affinity matured version or otherwise mutated version of 13C3, 1D1, 19A6 or other 13C3-like antibody. These nucleic acids are substantially free from other nucleic acids. For most cloning purposes, DNA is a preferred nucleic acid. These DNA molecules may be subcloned into an expression vector and subsequently transfected into a host cell of choice wherein the recombinant host cell provides a source for substantial levels of a relevant portion of the 13C3, 1D1, 19A6 or 13C3-, 1D1-, or 19A6-like antibody, or affinity matured version thereof. Such procedures may be used for a variety of utilities, such as generating scFvs or for co-expressing these $V_H$ and $V_L$ chains in a mammalian expression vector system which encodes human $C_H$ and $C_L$ regions, of say, an IgG antibody. The degeneracy of the genetic code is such that, for all but two amino acids, more than a single codon encodes a particular amino acid. This allows for the construction of synthetic DNA that encodes an antibody of the present invention where the nucleotide sequence of the synthetic DNA differs significantly from the nucleotide sequences disclosed herein, but still encodes such an antibody. Such synthetic DNAs are intended to be within the scope of the present invention. If it is desired to express such synthetic DNAs in a particular host cell or organism, the codon usage of such synthetic DNAs can be adjusted to reflect the codon usage of that particular host, thus leading to higher levels of expression of the an antibody of the present invention. In other words, this redundancy in the various codons which code for specific amino acids is within the scope of the present invention. Therefore, this invention is also directed to those DNA sequences which encode RNA comprising alternative codons which code for the eventual translation of the identical amino acid, as shown below: A=Ala=Alanine: codons GCA, GCC, GCG, GCU; C=Cys=Cysteine: codons UGC, UGU; D=Asp=Aspartic acid: codons GAC, GAU E=Glu=Glutamic acid: codons GAA, GAG; F=Phe=Phenylalanine: codons UUC, UUU; G=Gly=Glycine: codons GGA, GGC, GGG, GGU; H=His=Histidine: codons CAC, CAU; I=Ile=Isoleucine: codons AUA, AUC; AUU; K=Lys=Lysine: codons AAA, AAG; L=Leu=Leucine: codons UUA, UUG, CUA, CUC, CUG, CUU; M=Met=Methionine: codon AUG; N=Asp=Asparagine: codons GAU, GAC; P=Pro=Proline: codons CCA, CCC, CCG, CCU; Q=Gln=Glutamine: codons CAA, CAG; R=Arg=Arginine: codons AGA, AGG, CGA, CGC, CGG, CGU; S=Ser=Serine: codons AGC, AGU, UCA, UCC, UCG, UCU; T=Thr=Threonine: codons ACA, ACC, ACG, ACU; V=Val=Valine: codons GUA, GUC, GUG, GUU; W=Trp=Tryptophan: codon UGG; Y=Tyr=Tyrosine: codons UAC, UAU. Such recombinant expression vectors may then be stably or transiently transfected into an appropriate cell line for the generation of alternative antibody form.

The present invention notes the existence of codon redundancy which may result in differing DNA molecules expressing an identical antibody or portion thereof (e.g., alternative nucleic acid molecules encoding an identical scFv or a VH and/or VL portion of an IgG). For purposes of this specification, a sequence bearing one or more replaced codons will be defined as a degenerate variation. Another source of sequence variation may occur through RNA editing. Such RNA editing may result in another form of codon redundancy, wherein a change in the open reading frame does not result in an altered amino acid residue in the expressed protein. Also included within the scope of this invention are mutations either in the DNA sequence or the translated antibody which improve the ultimate physical properties of the expressed antibody. To this end, the present invention relates to (i) affinity matured versions of a 13C3-like antibody, including but not limited to 13C3, 19A6 and 1D1, and/or (ii) mutated forms of a 13C3-like antibody, including but not limited to 13C3, 19A6 and/or 1D1, including but not limited to one or more mutations in the CDR1, CDR2 an/or CDR3 regions as generated through known affinity maturation methodology and recombinant DNA techniques known for introducing site specific mutation. Such isolated or purified nucleic acid molecules will represent the VH and/or VL portions of a 13C3-like antibody. These nucleic acids are substantially free from other nucleic acids. For most cloning purposes, DNA is a preferred nucleic acid. These DNA molecules may be subcloned into an expression vector and subsequently transfected into a host cell of choice wherein the recombinant host cell provides a source for substantial levels of a relevant portion of a 13C3-like antibody, or affinity matured version thereof. Such procedures may be used for a variety of utilities, such as generating scFvs or for co-expressing these VH and VL chains in a mammalian expression vector system which encodes human CH and CL regions, of say, an IgG antibody.

The present invention also relates to recombinant vectors and recombinant hosts, both prokaryotic and eukaryotic, which contain nucleic acid molecules encoding the respective heavy and/or light regions of a 13C3-like antibody. These nucleic acid molecules, in whole or in part, can be linked with other DNA molecules (i.e., DNA molecules which encompass immunoglobulin genes used for generation of a recombinant human antibody) that are not naturally linked, to form "recombinant DNA molecules" which encode a respective human recombinant antibody. These vectors may be comprised of DNA or RNA. For most cloning purposes DNA vectors are preferred. Typical vectors include plasmids, modified viruses, bacteriophage, cosmids, yeast artificial chromosomes, and other forms of episomal or integrated DNA. It is within the purview of the skilled artisan to determine an appropriate vector for a particular gene transfer, generation of a recombinant human antibody or other use. Methods of subcloning nucleic acid molecules of interest into expression vectors, transforming or transfecting host cells containing the vectors, and methods of making substantially pure protein comprising the steps of introducing the respective expression vector into a host cell, and cultivating the host cell under appropriate conditions are well known. The antibody (such as an IgG recombinant human antibody) so produced may be harvested from the host cells in conventional ways. Any known expression vector may be utilized to practice this portion of the invention, including any vector containing a suitable promoter and other appropriate transcription regulatory elements. The resulting expression construct is transferred into a prokaryotic or eukaryotic host cell to produce recombinant protein. Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Techniques for such manipulations can be found described in Sambrook, et al. (1989, Molecular Cloning. A Laboratory Manual; Cold Spring Harbor Laboratory, Cold Spring Harbor, N.Y.) are well known and available to the artisan of ordinary skill in the art. Expression vectors may include, but are not limited to, cloning vectors, modified cloning vectors, specifically designed plasmids or viruses. Commercially available mammalian expression vectors which may be suitable, include but are not limited to, pcDNA3.neo (Invitrogen), pcDNA3.1 (Invitrogen), pCI-neo (Promega), pLITMUS28, pLITMUS29, pLITMUS38 and pLITMUS39 (New England Bioloabs), pcDNAI, pcDNA-Ianp (Invitrogen), pcDNA3 (Invitrogen), pMClneo (Stratagene), pXT1 (Stratagene), pSG5 (Stratagene), EBO pSV2-neo (ATCC 37593) pBPV-1 (8-2) (ATCC 37110), pdBPV-MMTneo (342-12) (ATCC 37224), pRSVgpt (ATCC 37199), pRSVneo (ATCC 37198), pSV2-dhfr (ATCC 37146), pUC-Tag (ATCC 37460), and 1ZD35 (ATCC 37565). Also, a variety of bacterial expression vectors are available, including but not limited to pCR2.1 (Invitrogen), pET11a (Novagen), lambda gt11 (Invitrogen), and pKK223-3 (Pharmacia). In addition, a variety of fungal cell expression vectors may be used, including but not limited to pYES2 (Invitrogen) and Pichie expression vector (Invitrogen). Also, a variety of insect cell expression vectors may be used, including but are not limited to pBlueBacIII and pBlueBacHis2 (Invitrogen), and pAcG2T (Pharmingen).

Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells. Mammalian species which may be suitable,-26 include but are not limited to, L cells L-M(TK-) (ATCCCCL1.3), L cells L-M (ATCC CCL 1.2), Saos-2 (ATCCHTB-85), 293 (ATCCCRL1573), Raji (ATCC CCL 86), CV-1 (ATCC CCL 70), COS-1 (ATCC CRL1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26), MRC-5 (ATCCCCL171) and CPAE (ATCC CCL 209).

Yet another improvement over re-engineered antibodies as reviewed above is the generation of fully human monoclonal antibodies. The first involves the use of genetically engineered mouse strains which possess an immune system whereby the mouse antibody genes have been inactivated and in turn replaced with a repertoire of functional human antibody genes, while leaving other components of the mouse immune system unchanged. Such genetically engineered mice allow for the natural in vivo immune response and affinity maturation process which results in high affinity, fully human monoclonal antibodies This technology is again now well known in the art and is fully detailed in various publications, including but not limited to U.S. Pat. Nos. 5,939,598; 6,075,181; 6,114,598; 6,150,584 and related family members (assigned to Abgenix, disclosing their XenoMouse technology); as well as U.S. Pat. Nos. 5,545,806; 5,569,825; 5,625, 126; 5,633,425; 5,789,650; 5,877, 397; 5,661,016; 5,814, 318; 5,874,299; and 5,770,429 (assigned to GenPharm International and available through Medarex, under the umbrella of the "UltraMab Human Antibody Development System"). See also a review from Kellerman and Green (2002, *Curr. Opinion in Biotechnology* 13: 593-597).

Finally, techniques are available to the artisan for the selection of antibody fragments from libraries using enrichment technologies, including but not limited to phage display, ribosome display (Hanes and Pluckthun, 1997, *Proc. Nat. Acad. Sci.* 94: 4937-4942), bacterial display (Georgiou, et al., 1997, *Nature Biotechnology* 15: 29-34) and/or yeast display (Kieke, et al., 1997, *Protein Engineering* 10: 1303-1310) may be utilized as alternatives to previously discussed technologies to select single chain antibodies which specifically bind to target cytokine. Single-chain antibodies are selected from a library of single chain antibodies produced directly utilizing filamentous phage technology. Phage display technology is known in the art (e.g., see technology from Cambridge Antibody Technology (CAT) as disclosed in U.S. Pat. Nos. 5,565, 332; 5,733,743; 5,871,907; 5,872,215; 5,885,793; 5,962,255; 6,140,471; 6,225,447; 6,291,650; 6,492,160; 6,521,404; 6,544,731; 6,555,313; 6,582,915; 6,593,081, as well as other U.S. family members, or applications which rely on priority filing GB 9206318, filed 24 May 1992; see also Vaughn, et al. 1996, *Nature Biotechnology* 14: 309-314). Single chain antibodies may also be designed and constructed using available recombinant DNA technology, such as a DNA amplification method (e.g., PCR), or possibly by using a respective hybridoma cDNA as a template. Single-chain antibodies can be mono- or bispecific; bivalent or tetravalent. A nucleotide sequence encoding a single-chain antibody can be constructed using manual or automated nucleotide synthesis, cloned into an expression construct using standard recombinant DNA methods, and introduced into a cell to express the coding sequence, as described below.

The present invention further relates to an antibody-based pharmaceutical composition comprising an effective amount a 13C3-like antibody, or an affinity matured version, which provides a prophylactic or therapeutic treatment choice to inhibit fibril and/or senile plaque formation associated with Alzheimer's disease. The antibody-based pharmaceutical composition of the present invention may be formulated by any number of strategies known in the art (e.g., see McGoff and Scher, 2000, *Solution Formulation of Proteins/Peptides*: In McNally, E. J., ed. *Protein Formulation and Delivery*. New York, N.Y.: Marcel Dekker; pp. 139-158; Akers and Defilippis, 2000, *Peptides and Proteins as Parenteral Solutions*. In: *Pharmaceutical Formulation Development of Peptides and Proteins*. Philadelphia, Pa.: Talyor and Francis; pp. 145-177; Akers, et al., 2002, *Pharm. Biotechnol.* 14:47-127). A pharmaceutically acceptable composition suitable for patient administration will contain an effective amount of the antibody in a formulation which both retains biological activity while also promoting maximal stability during storage within an acceptable temperature range. The pharmaceutical compositions can also include, depending on the formulation desired, pharmaceutically acceptable diluents, pharmaceutically acceptable carriers and/or pharmaceutically acceptable excipients, or any such vehicle commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. The amount of an excipient that is useful in the pharmaceutical composition or formulation of this invention is an amount that serves to uniformly distribute the antibody throughout the composition so that it can be uniformly dispersed when it is to be delivered to a subject in need thereof. It may serve to dilute the antibody to a concentration which provides the desired beneficial palliative or curative results while at the same time minimizing any adverse side effects that might occur from too high a concentration. It may also have a preservative effect. Thus, for the antibody having a high physiological activity, more of the excipient will be employed. On the other hand, for any active ingredient(s) that exhibit a lower physiological activity, a lesser quantity of the excipient will be employed. In general, the amount of excipient in the composition will be between about 50% weight (w) and 99.9% w. of the total composition. If the antibody exhibits a particularly low physiological activity, the amount of excipient could be as little as 1% w. On the other hand, for an antibody that has a particularly high physiological activity, the amount of excipient may be between about 98.0% and about 99.9% w. In addition, the antibody or antibodies may by administered in the form of a "chemical derivative" (a molecule that contains additional chemical moieties which are not normally a part of the base molecule). Such moieties may improve the solubility, half-life, absorption, etc. of the biological agent. Alternatively, these moieties may attenuate undesirable side effects of the antibody. Pharmaceutical compositions can also include large, slowly metabolized macromolecules such as proteins, polysaccharides, polylactic acids, polyglycolic acids and copolymers (such as latex functionalized sepharose, agarose, cellulose, and the like), polymeric amino acids, amino acid copolymers, and lipid aggregates (such as oil droplets or liposomes). Additionally, these carriers can function as immunostimulating agents (i.e., adjuvants). For parenteral administration, agents of the invention can be administered as injectable dosages of a solution or suspension of the substance in a physiologically acceptable diluent with a pharmaceutical carrier which can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

The antibody formulation may be in liquid form or solid form. A solid formulation is generally lyophilized and brought into solution prior to administration for either single or multiple dosing. The formulations should not be exposed to extreme temperature or pH so as to avoid thermal denaturation. Thus, it is essential to formulate an antibody composition of the present invention within a biologically relevant pH range. A solution buffered to maintain a proper pH range during storage is indicated, especially for liquid formulations stored for longer periods of time between formulation and administration. To date, both liquid and solid formulations require storage at lower temperatures (usually 2-8° C.) in order to retain stability for longer periods. Formulated antibody compositions, especially liquid formulations, may contain a bacteriostat to prevent or minimize proteolysis during storage, including but not linuted to effective concentrations (usually <1% w/v) of benzyl alcohol, phenol, m-cresol, chlorobutanol, methylparaben, and/or propylparaben. A bacteriostat may be contraindicated for some patients. Therefore, a lyophilized formulation may be reconstituted in a solution either containing or not containing such a component. Additional components may be added to either a buffered liquid or solid antibody formulation, including but not limited to sugars as a cryoprotectant (including but not necessarily limited to polyhydroxy hydrocarbons such as sorbitol, mannitol, glycerol and dulcitol and/or disaccharides such as sucrose, lactose, maltose or trehalose) and, in some instances, a relevant salt (including but not limited to NaCl, KCl or LiCl). Such antibody formulations, especially liquid formulations slated for long term storage, will rely on a useful range of total osmolarity to both promote long term stability at temperature of 2-8° C., or higher, while also making the formulation useful for parenteral injection. An effective range of total osmolarity (the total number of molecules in solution) is from about 200 mOs/L to about 800 mOs/L. It will be apparent that the amount of a cyroprotectant, such as sucrose or sorbitol, will depend upon the amount of salt in the formulation in order for the total osmolarity of the solution to remain within an appropriate range. Therefore a salt free formulation may contain from about 5% to about 25% sucrose, with a preferred range of sucrose from about 7% to about 15%, with an especially preferred sucrose concentration in a salt free formulation being from 10% to 12%. Alternatively, a salt free sorbitol-based formulation may contain sorbitol within a range from about 3% to about 12%, with a preferred range from about 4% to 7%, and an especially preferred range is from about 5% to about 6% sorbitol in a salt-free formulation. Salt-free formulations will of course warrant increased ranges of the respective cryoprotectant in order to maintain effective osmolarity levels. These formulation may also contain a divalent cation (including but not necessarily limited to $MgCl_2$, $CaCl_2$ and $MnCl_2$); and a non-32 ionic surfactant (including but not necessarily limited to Polysorbate-80 (Tween 80®), Polysorbate-60 (Tween 60®), Polysorbate-40 (Tween 40®) and Polysorbate-20 (Tween 20®), polyoxyethylene alkyl ethers, including but not limited to Brij 58®, Brij 35®, as well as others such as Triton X-100®, Triton X 114®, NP40®, Span 85 and the Pluronic series of non-ionic surfactants (e.g., Pluronic 121)). Any combination of such components, including probable inclusion of a bacteriostat, may be useful to fill the antibody-containing formulations of the present invention. The antibody composition of the present invention may also be a "chemical derivative", which describes an antibody that contains additional chemical moieties which are not normally a part of the immunogloblulin molecule (e.g., pegylation). Such moieties may improve the solubility, half-life, absorption, etc. of the base molecule. Alternatively the moieties may attenuate undesirable side effects of the base molecule or decrease the toxicity of the base molecule.

Numerous examples of various carriers, diluents, excipients and the such are known in the art and are disclosed in references cited herein, as well as *Remington's Pharmaceutical Sciences* (18th ed.; Mack Publishing Company, Easton, Pa., 1990), the contents of which are incorporated herein by reference. Briefly, it will be appreciated that suitable carriers, excipients, and other agents may be incorporated to formulate the pharmaceutical compositions to provide improved transfer, delivery, tolerance, and the like. The methods of incorporating the biological agent and/or additional active ingredient(s) into the carrier are known to a person of ordinary skill in the art and depend on the nature of the biological agent and the nature of the carrier selected by a person practicing the current invention. Ionic binding, gel encapsulation or physical trapping inside the carrier, iontophoresis and soaking the carrier in a solution of the biological agent are suitable examples contemplated in formulating a pharmaceutical composition to be used to practice of the disclosed treatment methods. Alternatively, the carrier may be little more than a diluent for the biological agent. These formulations may include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax. The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular biological agent thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug. Any of the foregoing formulations may be appropriate in treatments and therapies in accordance with the present invention, provided that the active ingredient in the formulation is not inactivated by the formulation and the formulation is physiologically compatible.

The pharmaceutical compositions of the present invention may be administered to the host in any manner, strategy and/or combination available in the art in amounts sufficient to offer a therapeutic treatment against Alzheimer's disease. These compositions may be provided to the individual by a variety of routes known in the art, especially parenteral routes, including but in no way limited to parenteral routes such as intravenous (IV), intramuscular (IM); or subcutaneous (SC) administration, with IV administration being the norm within the art of therapeutic antibody administration. These compositions may be administered as separate or multiple doses (i.e., administration of the antibody at staggered times by maintaining the sterile condition of the formulation through the treatment regime). The dosage regimen utilizing the compounds of the present invention is selected in accordance with a variety of factors including type, species, age, weight, sex and medical condition of the patient (such as a human patient); the severity of the condition to be treated; the route of administration; the renal, hepatic and cardiovascular function of the patient; and the particular antibody thereof employed. A physician or veterinarian of ordinary skill can readily determine and prescribe the effective therapeutic amount of the antibody. Optimal precision in achieving concentrations of antibody within the range that yields efficacy without toxicity requires a regimen based on the kinetics of the drug's availability to target sites. This involves a consideration of the distribution, equilibrium, and elimination of a drug. Antibodies described herein may be used alone at appropriate dosages. Alternatively, co-administration or sequential administration of other agents may be desirable. It will be possible to present a therapeutic dosing regime for the antibodies of the present invention in conjunction with administration of alternative prophylactic or therapeutic regimes. An effective dosage regime will vary depending upon many different factors, including means of administration, target site, physiological state of the patient, whether the patient is human or an animal, other medications administered, and whether treatment is prophylactic or therapeutic. For administration of a 13C3-like antibody, the dosage ranges from about 0.0001 to 100 mg/kg, and more usually 0.01 to 5 mg/kg of the host body weight. In the case of Alzheimer's disease, amyloid deposits occur in the brain, agents of the invention can also be administered in conjunction with other agents that increase passage of the agents of the invention across the blood-brain barrier.

Another aspect regarding delivery and dosage regimes for a 13C3-like antibody composition of the present invention relates to drug delivery via parenteral routes, which may include non-injectable and injectable devices. Typically, injectable compositions are prepared as either liquid solutions or suspensions; solid forms suitable for solution in, or suspension in, liquid vehicles prior to injection can also be prepared. The preparation also can be emulsified or encapsulated in liposomes or microparticles such as polylactide, polyglycolide, or copolymer for enhanced adjuvant effect, as discussed above (see Langer, 1990, *Science* 249: 1527-1523; and Hanes, 1997, *Advanced Drug Delivery Reviews* 28: 97-119). The agents of this invention can be administered in the form of a depot injection or implant preparation which can be formulated in such a manner as to permit a sustained or pulsatile release of the active ingredient.

Specific embodiments include PLGA microspheres, as discussed herein and as further known in the art, as well as polymer-based non-degradable vehicles comprising poly (ethylene-co-vinyl acetate; PEVAc). Additionally, controlled-release and localized delivery of antibody-based therapeutic products is reviewed in Grainger, et al., 2004, *Expert Opin. Biol. Ther.* 4(7): 1029-1044), hereby incorporated by reference in its entirety. Suitable microcapsules capable of encapsulating the antibody may also include hydroxymethylcellulose or gelatin-microcapsules and polymethyl methacrylate microcapsules prepared by coacervation techniques or by interfacial polymerization. See PCT publication WO 99/24061 entitled "Method for Producing IGF-1 Sustained-Release Formulations," wherein a protein is encapsulated in PLGA microspheres, this reference which is hereby incorporated herein by reference in its entirety. In addition, microemulsions or colloidal drug delivery systems such as liposomes and albumin microspheres, may also be used. Other preferred sustained-release compositions employ a bioadhesive to retain the antibody at the site of administration. As noted above, the sustained-release formulation may comprise a biodegradable polymer into which the antibody is disposed, which may provide for non-immediate release. Non-injectable devices may be described herein as an "implant", "pharmaceutical depot implant", "depot implant", "non-injectable depot" or some such similar term. Common depot implants may include, but are not limited to, solid biodegradable and non-biodegradable polymer devices (such as an extended polymer or coaxial rod shaped device), as well as numerous pump systems also known in the art. Injectable devices are split into bolus injections (release and dissipation of the drug subsequent to injection), and repository or depot injections, which provide a storage reservoir at the site of injection, allowing for sustained-release of the biological agent over time. A depot implant may be surgically tethered to the point of delivery so as to provide an adequate reservoir for the prolonged release of the antibody over time. Such a device will be capable of carrying the drug formulation in such quantities as therapeutically or prophylactically required for treatment over the pre-selected period. The depot implant may also provide protection to the formulation from degradation by body processes (such as proteases) for the duration of treatment. As known in the art, the term "sustained-release" refers to the gradual (continuous or discontinuous) release of such an agent from the block polymer matrix over an extended period of time. Regardless of the specific device, the sustained-release of the 13C3-like antibody composition will result in a local, biologically effective concentrations of the antibody. A sustained release of the biological agent(s) will be for a period of a single day, several days, a week or more; but most likely for a month or more, or up to about six months, depending on the formulation. Natural or synthetic polymers known in the art will be useful as a depot implant due to characteristics such as versatile degradation kinetics, safety, and biocompatibility. These copolymers can be manipulated to modify the pharmacokinetics of the active ingredient, shield the agent from enzymatic attack, as well as degrading over time at the site of attachment or injection. The artisan will understand that there are ample teachings in the art to manipulate the properties of these copolymers, including the respective production process, catalysts used, and final molecular weight of the sustained-release depot implant or depot injection. Natural polymers include but are not limited to proteins (e.g., collagen, albumin or gelatin); polysaccharides (cellulose, starch, alginates, chitin, chitosan, cyclodextrin, dextran, hyaluronic acid) and lipids. Biodegradable synthetic polymers may include but are not limited to various polyesters, copolymers of L-glutamic acid and gamma ethyl-L-glutamate (Sidman et al., 1983, Biopolymers 22:547-556), polylactides ([PLA]; U.S. Pat. No. 3,773,919 and EP 058, 481), polylactate polyglycolate (PLGA) such as polylactide-co-glycolide (see, for example, U.S. Pat. Nos. 4,767,628 and 5,654,008), polyglycolide (PG), polyethylene glycol (PEG) conjugates of poly(α-hydroxy acids), polyorthoesters, polyaspirins, polyphosphagenes, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, polyorthoesters (POE), or any combinations thereof, as described above (see, for example, U.S. Pat. No. 6,991,654 and U.S. Pat. Appl. No. 20050187631, each of which is incorporated herein by reference in its entirety, hydrogels (see, for example, Langer et al., 1981, J. Biomed. Mater. Res. 15:167-277; Langer, 1982, Chem. Tech. 12:98-105, non-degradable ethylene-vinyl acetate (e.g. ethylene vinyl acetate disks and poly(ethylene-co-vinyl acetate)), degradable lactic acid-glycolic acid copolyers such as the Lupron Depot™, poly-D-(−)-3-hydroxybutyric acid (EP 133, 988), hyaluronic acid gels (see, for example, U.S. Pat. No. 4,636,524), alginic acid suspensions, polyorthoesters (POE), and the like. Polylactide (PLA) and its copolymers with glycolide (PLGA) have been well known in the art since the commercialization of the Lupron Depot™, approved in 1989 as the first parenteral sustained-release formulation utilizing PLA polymers. Additional examples of products which utilize PLA and PLGA as excipients to achieve sustained-release of the active ingredient include Amidox (PLA; periodontal disease), Nutropin Depot (PLGA; with hGH), and the Trelstar Depot (PLGA; prostate cancer). Other synthetic polymers included but are not limited to poly(c-caprolactone), poly3-hydroxybutyrate, poly(β-malic acid) and poly (dioxanone)]; polyanhydrides, polyurethane (see WO 2005/013936), polyamides, cyclodestrans, polyorthoesters, n-vinyl alcohol, polyethylene oxide/polyethylene terephthalate, polyphosphazene, polyphosphate, polyphosphonate, polyorthoester, polycyanoacrylate, polyethylenegylcol, polydihydropyran, and polyacytal. Non-biodegradable devices include but are not limited to various cellulose derivatives (carboxymethyl cellulose, cellulose acetate, cellulose acetate propionate, ethyl cellulose, hydroxypropyl methyl cellulose) silicon-based implants (polydimethylsiloxane), acrylic polymers, (polymethacrylate, polymethylmethacrylate, polyhydroxy(ethylmethylacrylate), as well as polyethylene-co-(vinyl acetate), poloxamer, polyvinylpyrrolidone, poloxamine, polypropylene, polyamide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-a-chloro-p-xylene, polymethylpentene, polysulfone and other related biostable polymers. Carriers suitable for sustained-release depot formulations include, but are not limited to, micospheres, films, capsules, particles, gels, coatings, matrices, wafers, pills or other pharmaceutical delivery compositions. Examples of such sustained-release formulations are described above. See also U.S. Pat. Nos. 6,953,593; 6,946, 146; 6,656,508; 6,541,033; and 6,451,346, the contents of each which are incorporated herein by reference. The dosage form must be capable of carrying the drug formulation in such quantities and concentration as therapeutically required for treatment over the pre-selected period, and must provide sufficient protection to the formulation from degradation by body processes for the duration of treatment. For example, the dosage form can be surrounded by an exterior made of a material that has properties to protect against degradation from metabolic processes and the risk of, e.g., leakage, cracking, breakage, or distortion. This can prevent expelling of the dosage form contents in an uncontrolled manner under stresses it would be subjected to during use, e.g., due to physical forces exerted upon the drug release device as a result of normal joint articulation and other movements by the subject or for example, in convective drug delivery devices, physical forces associated with pressure generated within the reservoir. The drug reservoir or other means for holding or containing the drug must also be of such material as to avoid unintended reactions with the active agent formulation, and is preferably biocompatible (e.g., where the dosage form is implanted, it is substantially non-reactive with respect to a subject's body or body fluids). Generally, the respective biological agent(s) is administered to an individual for at least 12 hours to at least a week, and most likely via an implant designed to deliver a drug for at least 10, 20, 30, 100 days or at least 4 months, or at least 6 months or more, as required. The 13C3-like antibody can be delivered at such relatively low volume rates, e.g., from about 0.001 ml/day to 1 ml/day so as to minimize tissue disturbance or trauma near the site where the formulation is released. The formulation may be released at a rate of, depending on the specific biological agent(s), at a low dose, e.g., from about 0.01 μg/hr or 0.1 μg/hr, 0.25 μg/hr, 1 μg/hr, generally up to about 200 μg/hr, or the formulation is delivered at a low volume rate e.g., a volume rate of from about 0.001 ml/day to about 1 ml/day, for example, 0.01 micrograms per day up to about 20 milligrams per day. Dosage depends on a number of factors such as potency, bioavailability, and toxicity of the active ingredient (e.g., IgG antibody) used and the requirements of the subject.

These and other objects, advantages and features of the present invention will become apparent to those persons skilled in the art upon reading the details of the methodology and compositions as more fully set forth below.

EXAMPLES

Example 1

Preparing the Protofibrillar Form of Amyloid Beta (Aβ42)

Aβ42 synthetic peptides (American Peptide Company, Inc., CA) were prepared according to the method described by Fezoui et al. (Fezoui, et al. Amyloid 7(3): 166-178. (2000)) Briefly, lyophilized Aβ42 was dissolved in 2 mM NaOH at a 1 mg/ml concentration (pH~10.5) followed by sonication and lyophilization. NaOH-treated Aβ was dissolved in water at a concentration of 1 mg/ml and filtered with a 0.22 μm ULTRAFREE-MC filter (Millipore, Mass.). A 0.5 mg/ml peptide solution was buffered at the final concentration of 50 mM phosphate; 100 mM sodium chloride and incubated for 4 hr. at room temperature. To separate the protofibrillar form from the low-molecular weight proteins, the supernatant was fractionated using size-exclusion chromatography. Purified SEC fractions were then stored at 4C°.

Various forms of the Aβ42 protein are represented as showing its ability as a monomer or dimer to associate together to form a high-molecular weight oligomer (protofibril) (FIG. 1). Further aggregation of the soluble protofibrils creates an insoluble form of the protein, whereas the protofibrils can disassociate back to a lower-molecular weight form.

Figure 2:
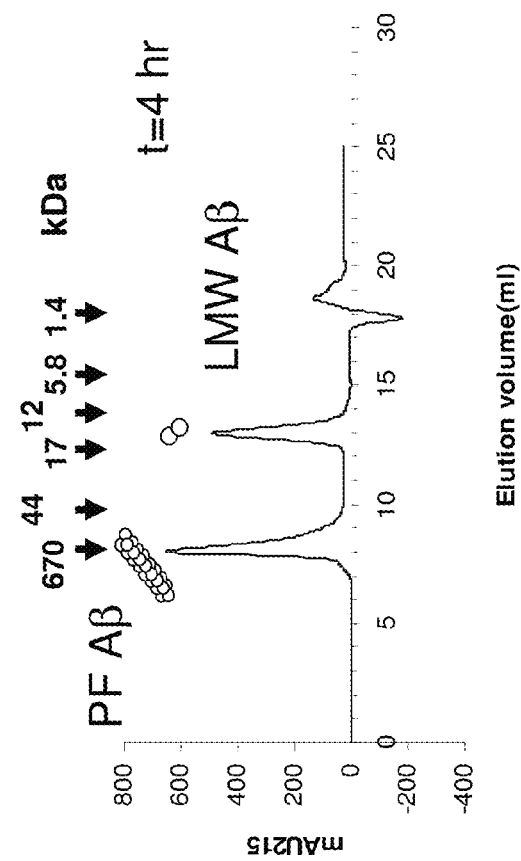
FIG. 2A-B show the process of Aβ fibrillogenesis and purification of Aβ forms at time 0 (A) and 4 hours (B) as indicated by absorbance at $mAU_{215}$ (absorbance @ 215 nm) for elution volumes. At 4 hours (B), the low molecular weight (LMW) form elutes as a ~15 kDa dimer while the protofibril form size elutes at ~670 kDa.
Figure 2:
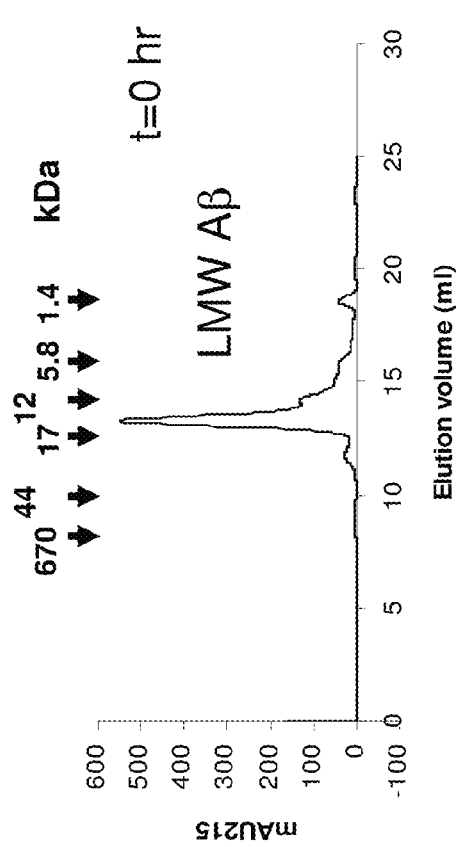

To purify the protofibrillar form of Aβ from the low-molecular weight proteins, samples were fractionated with an AKTA chromatography system using a Superdex 75 size-exclusion column. FIG. 2A shows that without incubating the A☐ 42 synthetic peptides at room temperature, there is no aggregation of oligomers to form the protofibrils. FIG. 2B illustrates that after a 4 hr. incubation of the Aβ42 synthetic peptides, subsequent SEC purification shows a definitive protofibril fraction.

Example 2

Generating Monoclonal Antibodies with Specificity for Protofibrillar Aβ

The 13C3, 19A6, and 1D1 antibodies were created by immunizing Balb/c mice with the fibrilliar Aβ protein using a protocol known in the art. (Harlow, et al. Cold Spring Harbor Laboratory.(1988)) Spleens were removed and fused with SP2 myeloma cells in several 96 well plates. Fusion cultures were monitored for growth and supernatants were screened for their ability to bind the protofibrilliar fraction by antibody-capture immunoassays.

Example 3

Characterization of Monoclonal Antibodies with Specificity for Protofibrillar Aβ

Antibody capture assays were used to further characterize the monoclonal antibodies produced from the hybridomas (13C3, 19A6, and 1D1). To microtiter plates, 50 ul of a 2 ug/ml protofibrillar Aβ42 protein solution was added to each well and the plates were incubated at 4° C. overnight. After incubation, the residual antigen solution was removed and washed with PBS solution. Serial dilutions of the hybridoma supernatants were added to the plates containing the bound antigen and incubated for 1 hour at room temperature. This primary antibody solution was removed and the wells were again washed with PBS solution. An enzyme-labeled secondary antibody was next added and incubated for 1 hour at room temperature. After removal of the secondary antibody solution, a chromogenic substrate specific for the conjugated enzyme, was added to the reaction and the detection of the captured antibody yielded quantitative results.

Additionally, changing the secondary reagent to isotype-specific anti-immunoglobulin antibodies, the particular immunoglobulin isotype of each monoclonal was identified. In these experiments, commercially available anti-Aβ42 antibodies were used to compare the binding specificity of 13C3, 19A6, and 1D1 monoclonal antibodies.

Figure 3:
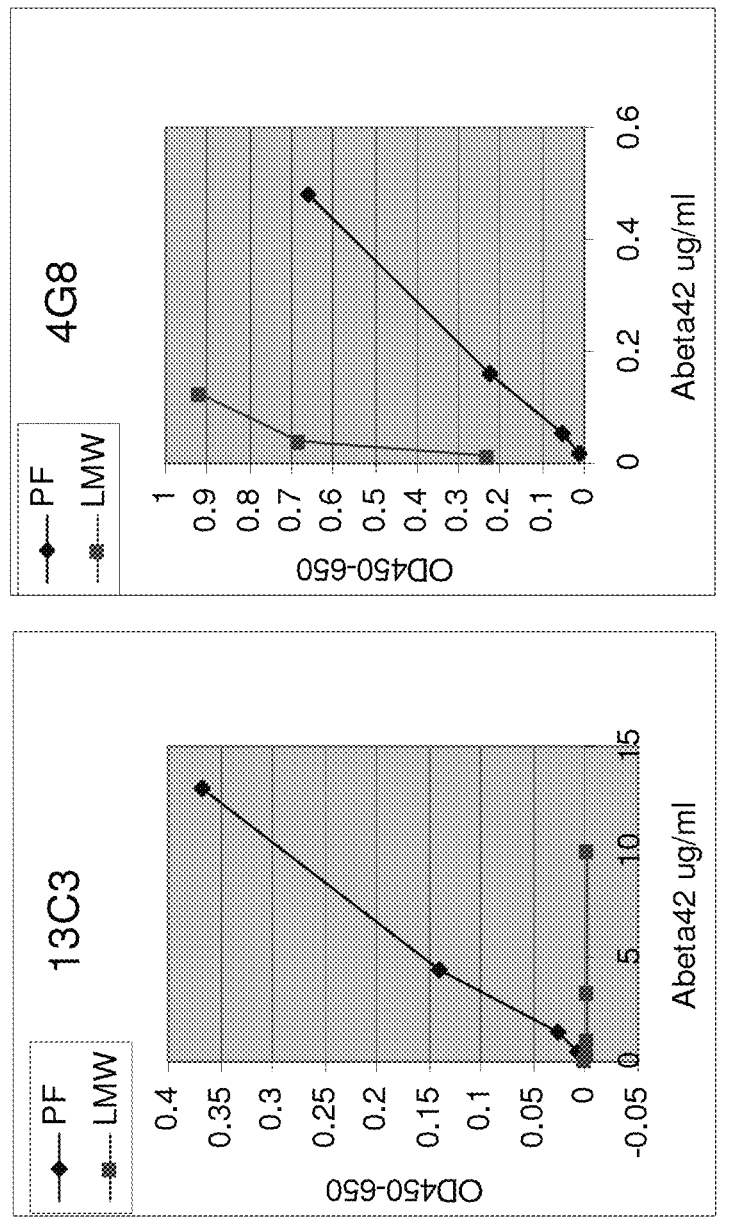
FIG. 3A-B show the specificity of monoclonal antibodies 13C3 (A) and 4G8 (B) for the protofibril (PF:-♦-) and low molecular weight (LMW: -■-) forms of Aβ, as indicated by optical density (OD) read at 450/650 nm for increasing concentrations of both the PF and LMW forms of Aβ.

FIGS. 3A and B illustrate the protofibrillar (PF) and the low-molecular weight (LMW) forms of the Aβ42 peptide used to test the specificity of the 13C3 antibody in antibody capture immunoassays. Specifically, FIG. 3A illustrates the plot generated from the ELISAs showing that the 13C3 antibody is specific for the protofibrillar form(PF) of Aβ42 and does not recognize the low-molecular weight(LMW) forms of the protein.

FIG. 3B illustrates the ELISA data with the commercially available 4G8 antibody, showing that it recognizes both the low-molecular weight and the protofibrillar forms of the Aβ42 protein.

Example 4

Specificity of Monoclonal Antibodies to the Protofibrillar Form of Aβ42 Using Surface Plasmon Resonance (bIACORE).

The purified monoclonal antibodies listed in Table 1 (below), were immobilized to a BIAcore sensor chip in accordance with publish protocols. (Nice, et al. BioEssays 21: 339-352 (1999)). The high sensitivity of the BIAcore optical response quantifies a change in reflectivity and a baseline response for the ligand alone is generated. The interaction analysis is performed as the analytes, the LMW form or the PF form of Aβ42, are injected in solution over the sensor chip and the change in surface plasmon resonance generates a response identifying the specificity of each antibody's ability to bind LMW and PF Aβ42. Both the 13C3 and the 19A6 antibodies all bound to the PF form of Aβ 42 with higher specificity than the LMW form. Of all the antibodies used in this experiment, the commercially-available antibodies showed higher specificity for the LMW Aβ42 over the PF form of Aβ 42, as indicated the ratio of PF binding/LMW binding.

TABLE 1

| | | | | BIACORE Binding Analysis | | |
|---|---|---|---|---|---|---|
| Name | Epitope | Isotype | Source | LMW | PF | Ratio (PF/LMW) |
| 1D1 | structure | IgG1 | Ravetch | 23.2 | 122.3 | 5.3 |
| 13C3 | structure | IgG1 | Ravetch | 25 | 124.8 | 5.0 |
| 19A6 | structure | IgG3 | Ravetch | | | |
| 3D6 | Aβ 1-5 | IgG2b | Elan Pharmaceuticals | 424.6 | 402.7 | 0.9 |
| 4G8 | Aβ 17-22 | IgG2b | Senetek Inc. | 228.6 | 340.3 | 1.5 |
| 6E10 | Aβ 3-8 | IgG2b | Senetek Inc. | 400.1 | 541.1 | 1.4 |
| 82E1 | Aβ 1-17 | IgG1 | IBL | 69.9 | 68.4 | 1.0 |

Figure 4:
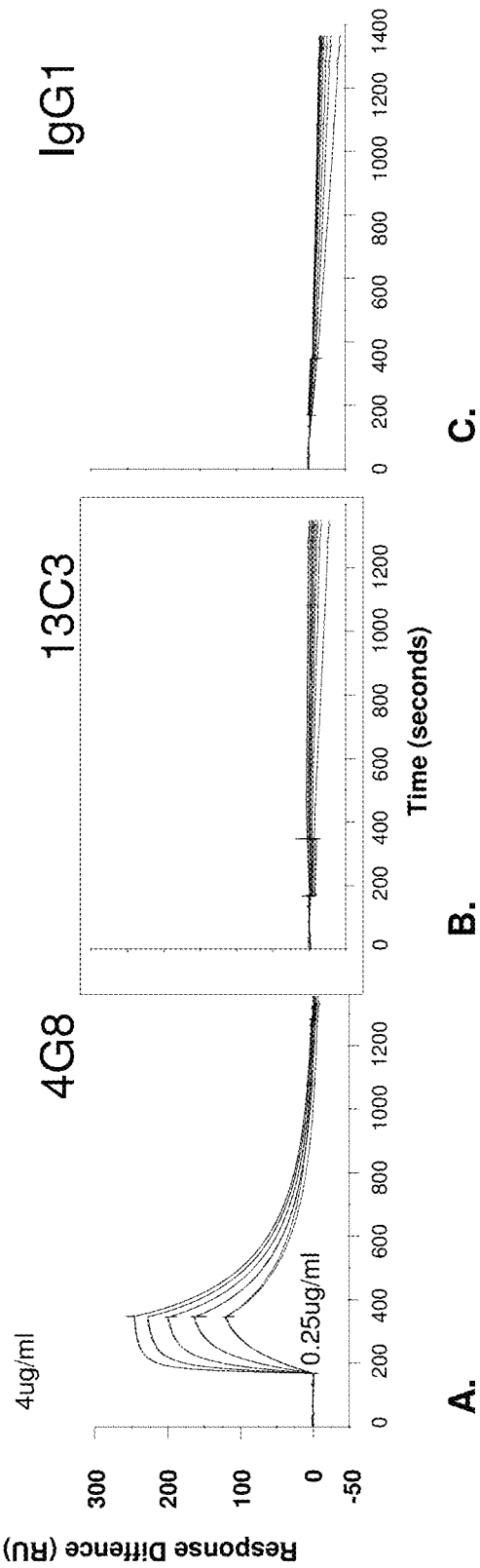
FIG. 4A-C show data from a Biacore° binding assay showing affinity of monoclonal antibodies 4G8 (A), 13C3 (B) and control $IgG_1$ (C) to varying concentrations of low molecular weight (LMW) form of Aβ from 0.25 μg/ml LMW Aβ to 4.0 μg/ml LMW Aβ.

The Surface Plasmon Resonance Analysis shown by sensorgram that 13C3 (FIG. 4B) does not bind the LMW forms of Aβ 42 protein. However, the 4G8 (FIG. 4A) shows a standard association/disassociation curve for the LMW Aβ42 protein. The antibody isotype control IgG1 (Figure C) does not bind the LMW Aβ as well. Automated BIAcore systems, which use the detection principle of Surface Plasmon Resonance, were used in these experiments. The binding specificity data for the 19A6 antibody showed that 19A6 had a binding ratio of 5.8, which is similar to that of 13C3 at a ratio of 5.3.

Example 5

Epitope Mapping of the 13C3 Antibody

Mapping the epitopes of 13C3, 1D1 and 19A6 was conducted using the RepliTope Microarrays system (JPT Peptide Technologies GmbH) according to published protocol. (Korth, et al. 390: 74 (1997)). Each spot on the microarray contains a 13 amino acid peptide of Aβ42 where each shift in position on the microarray represents an amino acid shift (fom N-term to C-term), i.e. SEQ ID NO: 23, SEQ ID NO: 24, SEQ ID NO: 51; and SEQ ID NO: 52. Listed below are the peptides and their exact amino acid sequence, corresponding to their position on the slide array. Once the peptides are fixed to the RepliTope Microarray, the samples are incubated with the 13C3 antibody and then subsequently labeled with a secondary that is conjugated to a chemiluminescence tag of choice. The spots that yield a signal represent the epitope binding sites on the protein by the antibody.

(SEQ ID NO: 23)
Asp Ala Glu Phe Arg His Asp Ser Gly Tyr Glu Val His (SEQ ID NO: 24)
Ala Glu Phe Arg His Asp Ser Gly Tyr Glu Val His His (SEQ ID NO: 25)
Glu Phe Arg His Asp Ser Gly Tyr Glu Val His His Gln (SEQ ID NO: 26)
Phe Arg His Asp Ser Gly Tyr Glu Val His His Gln Lys (SEQ ID NO: 27)
Arg His Asp Ser Gly Tyr Glu Val His His Gln Lys Leu (SEQ ID NO: 28)
His Asp Ser Gly Tyr Glu Val His His Gln Lys Leu Val (SEQ ID NO: 29)
Asp Ser Gly Tyr Glu Val His His Gln Lys Leu Val Phe (SEQ ID NO: 30)
Ser Gly Tyr Glu Val His His Gln Lys Leu Val Phe Phe (SEQ ID NO: 31)
Gly Tyr Glu Val His His Gln Lys Leu Val Phe Phe Ala (SEQ ID NO: 32)
Tyr Glu Val His His Gln Lys Leu Val Phe Phe Ala Glu (SEQ ID NO: 33)
Glu Val His His Gln Lys Leu Val Phe Phe Ala Glu Asp (SEQ ID NO: 34)
Val His His Gln Lys Leu Val Phe Phe Ala Glu Asp Val (SEQ ID NO: 35)
His His Gln Lys Leu Val Phe Phe Ala Glu Asp Val Gly (SEQ ID NO: 36)
His Gln Lys Leu Val Phe Phe Ala Glu Asp Val Gly Ser (SEQ ID NO: 37)
Gln Lys Leu Val Phe Phe Ala Glu Asp Val Gly Ser Asn (SEQ ID NO: 38)
Lys Leu Val Phe Phe Ala Glu Asp Val Gly Ser Asn Lys (SEQ ID NO: 39)
Leu Val Phe Phe Ala Glu Asp Val Gly Ser Asn Lys Gly (SEQ ID NO: 40)
Val Phe Phe Ala Glu Asp Val Gly Ser Asn Lys Gly Ala (SEQ ID NO: 41)
Phe Phe Ala Glu Asp Val Gly Ser Asn Lys Gly Ala Ile

-continued

Phe Ala Glu Asp Val Gly Ser Asn Lys Gly Ala (SEQ ID NO: 42)
Ile Ile

Ala Glu Asp Val Gly Ser Asn Lys Gly Ala Ile (SEQ ID NO: 43)
Ile Gly

Glu Asp Val Gly Ser Asn Lys Gly Ala Ile Ile (SEQ ID NO: 44)
Gly Leu

Asp Val Gly Ser Asn Lys Gly Ala Ile Ile Gly (SEQ ID NO: 45)
Leu Met

Val Gly Ser Asn Lys Gly Ala Ile Ile Gly Leu (SEQ ID NO: 46)
Met Val

Gly Ser Asn Lys Gly Ala Ile Ile Gly Leu Met (SEQ ID NO: 47)
Val Gly

Ser Asn Lys Gly Ala Ile Ile Gly Leu Met Val (SEQ ID NO: 48)
Gly Gly

Asn Lys Gly Ala Ile Ile Gly Leu Met Val Gly (SEQ ID NO: 49)
Gly Val

Lys Gly Ala Ile Ile Gly Leu Met Val Gly Gly (SEQ ID NO: 50)
Val Val

Gly Ala Ile Ile Gly Leu Met Val Gly Gly Val (SEQ ID NO: 51)
Val Ile

Ala Ile Ile Gly Leu Met Val Gly Gly Val Val (SEQ ID NO: 52)
Ile Ala

Figure 5:
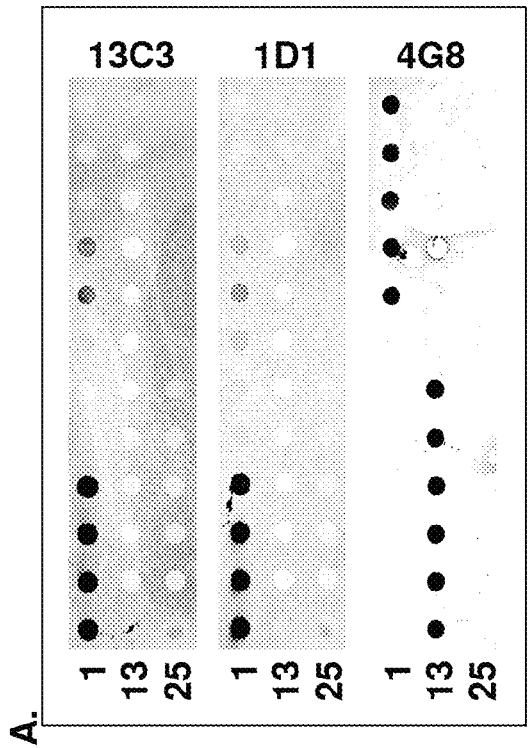
FIG. 5A-B show data identifying the epitopes recognized by the anti-Aβ antibodies described above.
Figure 5:
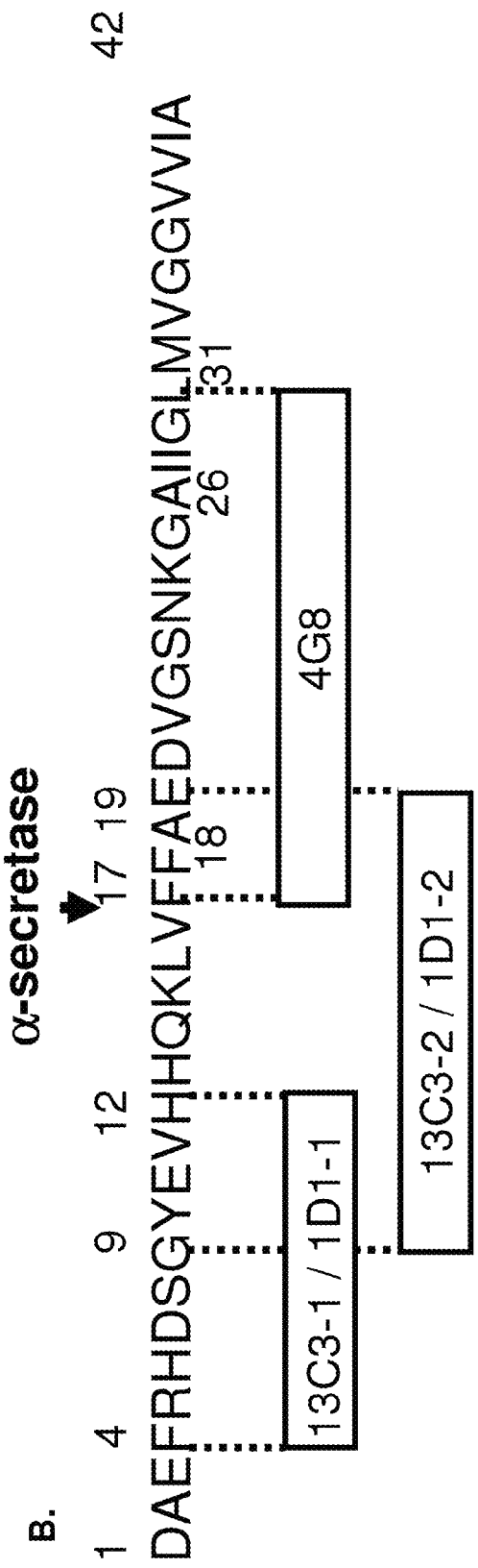

FIG. 5A illustrates a dot blot from a RepliTope Microarray experiment identifying the epitopes of the antibodies, 13C3, 1D1 and 4G8 on the Aβ 1-42 peptide. The bound antibody is represented by a chemiluminescent signal. FIG. 5B illustrates the Aβ 1-42 amino acid sequence showing the polypeptide segments of the 13C3 epitopes as they occur in the sequence. The 1D1 antibody shows the same epitopes as the 13C3 whereas the commercial 4G8 antibody identifies a different epitope.

Example 6

Characterization of 13C3 Specificity

Figure 6:
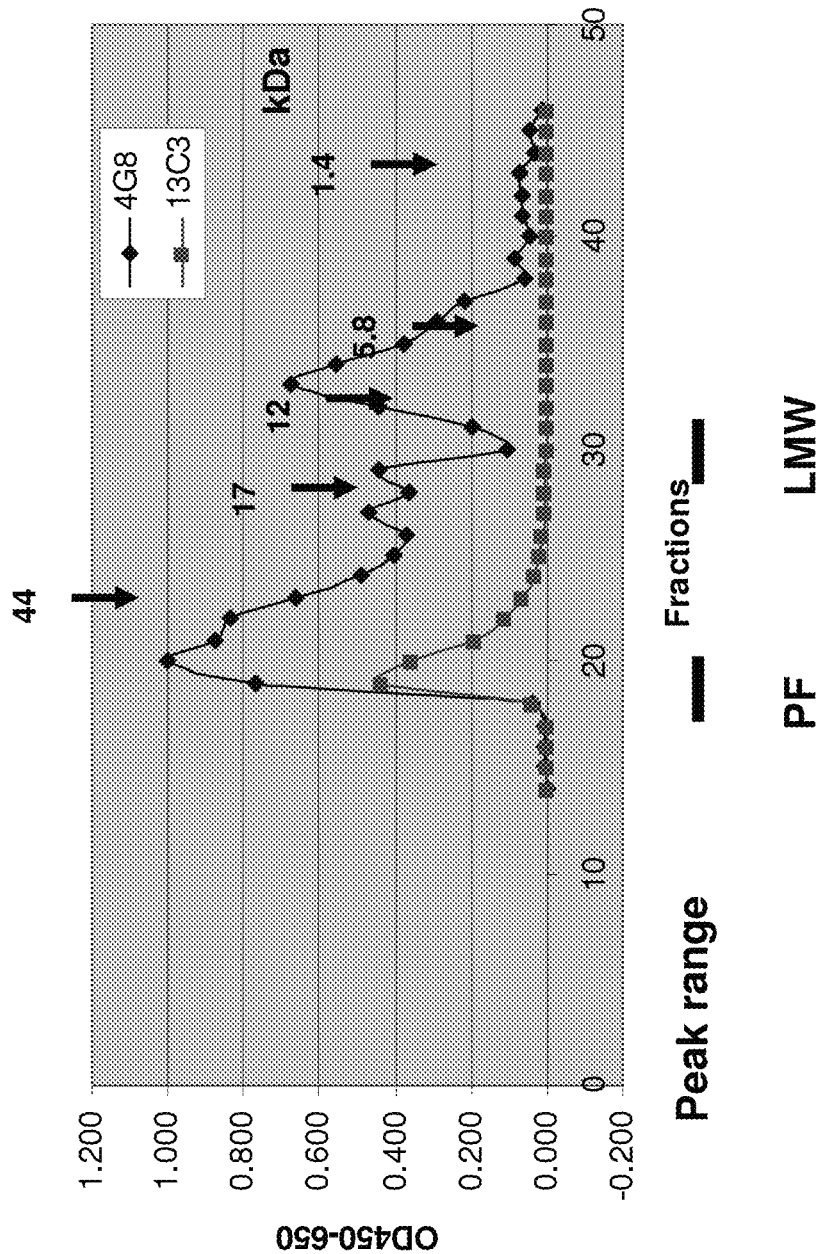
FIG. 6 shows the reactivity of monoclonal antibodies 13C3 (-■-) and 4G8 (-♦-) with SEC fractions from 7PA2 supernatant secreting Aβ oligomers. Protofibril (PF) and low molecular weight (LMW) fractions are indicated on the x-axis as measured by optical density (OD) read at 450/650.

FIG. 6 illustrates fractions from size-exclusion chromatography of the supernatants from the 7PA2 cell line, a secreting Aβ oligomer cell line. Antibody capture assays were used to further characterize the binding of the 13C3 antibody with the protofibrillar and low-molecular weight fractions from the SEC-purified 7PA2. To microtiter plates, 100 ul of a 1:200 dilution of each fraction was added to each well and the plates were incubated at 4° C. overnight. After incubation, the residual antigen solution was removed and washed with PBS solution. Serial dilutions of the 13C3 supernatants were added to the plates containing the bound antigen and incubated for 1 hour at room temperature. This primary antibody solution was removed and the wells were again washed with PBS solution. An enzyme-labeled secondary antibody was next added and incubated for 1 hour at room temperature. After removal of the secondary antibody solution, a chromogenic substrate specific for the conjugated enzyme, was added to the reaction and the detection of the captured antibody yielded quantitative results. This assay identified that the 13C3 antibody specifically recognizes only the protofibrillar fraction whereas the 4G8 antibody recognizes all fractions. The 7PA2 cell line was provided by Dennis J. Selkoe, M.D. at Harvard Medical School.

Example 7

Characterization of 13C3 Reactivity by EM

The method of staining was performed using a standard protocol. (Brenner, et al. Biochim. Biophys. Ada 34, 103-110 (1959)). A small volume (10 microliters) of a 0.2 mg/ml protofibrillar solution was applied to carbon-coated formvar grids (400 mesh) for 2 min. Then the grids were blocked in 1% BSA and incubated with the 13C3 antibody followed by a subsequent incubation with a secondary antibody conjugated to colloidal gold. The samples were negatively stained by placing on 2 successive drops of 2% phosphotungstic acid for 30 sec each. Excess stain was drawn off with filter paper, the grids were air dried, and observed on a JEOL 100CX transmission electron microscope at 80 kV. Images were recorded on large format Kodak 4489 negatives and digitized on a flat bed scanner.

Figure 7:
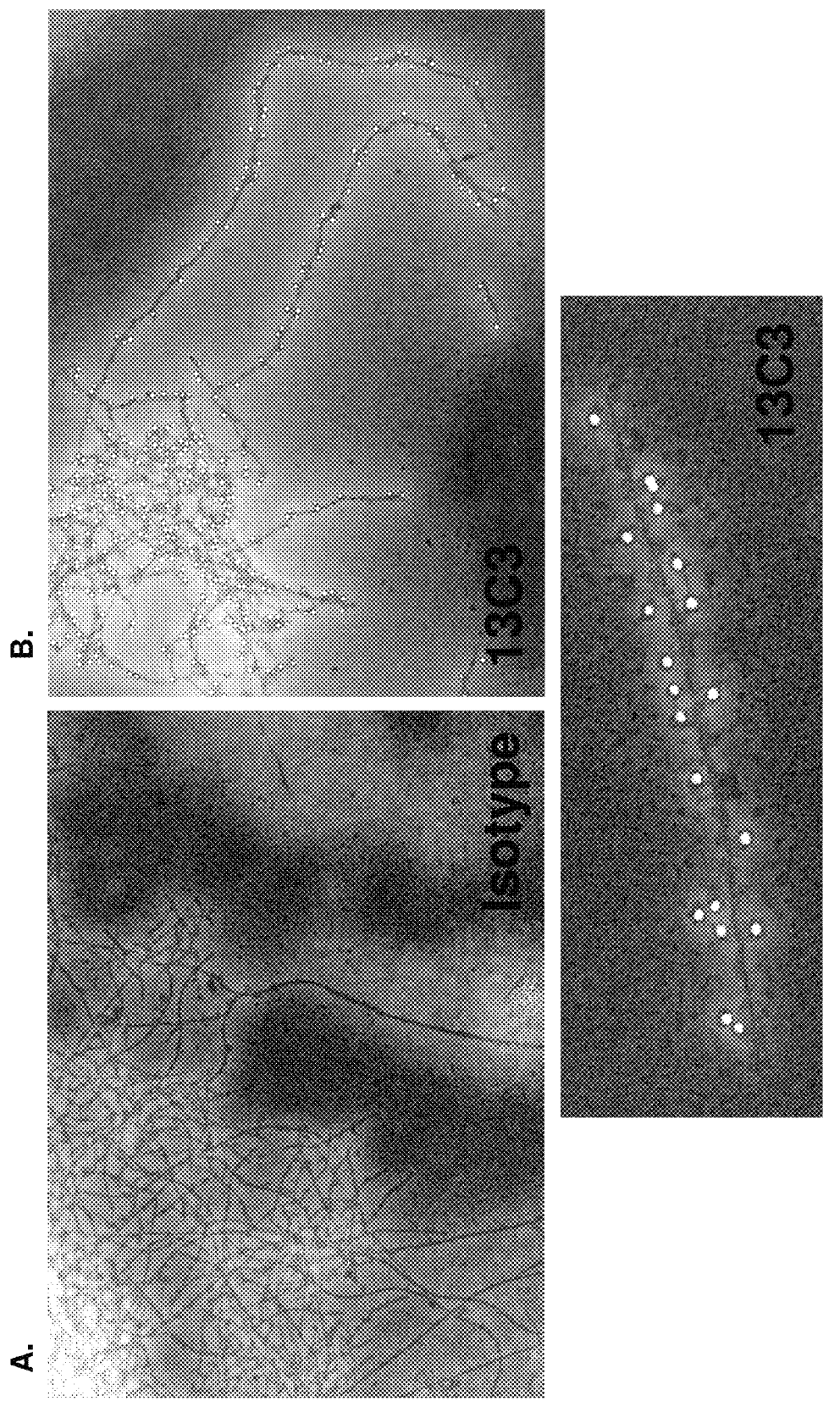
FIGS. 7A-C show micrographs from thin section immuno-electron microscopy showing the affinity of monoclonal antibody 13C3 to repeated structures on Aβ fibrils (B, C). Control immuno-EM is $IgG_1$ (A).

IEM (Immuno-Electron Microscopy) images showing the binding specificity of the anti-Aβ antibody clone 13C3 to Aβ42 fibers (FIGS. 7B and 7C), whereas the isotype control antibody, IgG1 shows no binding (FIG. 7A). The secondary antibody is conjugated to a colloidal gold particle.

Example 8

13C3 Treatment of a Mouse Model of Human Ad

The 13C3 monoclonal antibody was used to treat Aβ plaques in an Alzheimer's Disease mouse model, TgCRND8. The mouse contains the human APP695 cDNA transgene, which accelerates the deposition of Aβ amyloid plaques in the mouse brain, appearing within 1 month of age. A sample group of 5 TgCRND8 mice five weeks in age were give immunizations of the 13C3 monoclonal antibody at a concentration of 10 mg/kg of mouse once a week for the duration of seven weeks. A second group of 5 TgCRND8 mice, were given the treatment course, however an isotype control IgG1 antibody was administered. Experiments were repeated with treatments at twice a week instead of once a week.

Both control and experimental animals were sacrificed at 12 weeks of age. Histological preparations of the brains revealed reductions in Aβ plaques in 13C3 treated mice.

Figure 8:
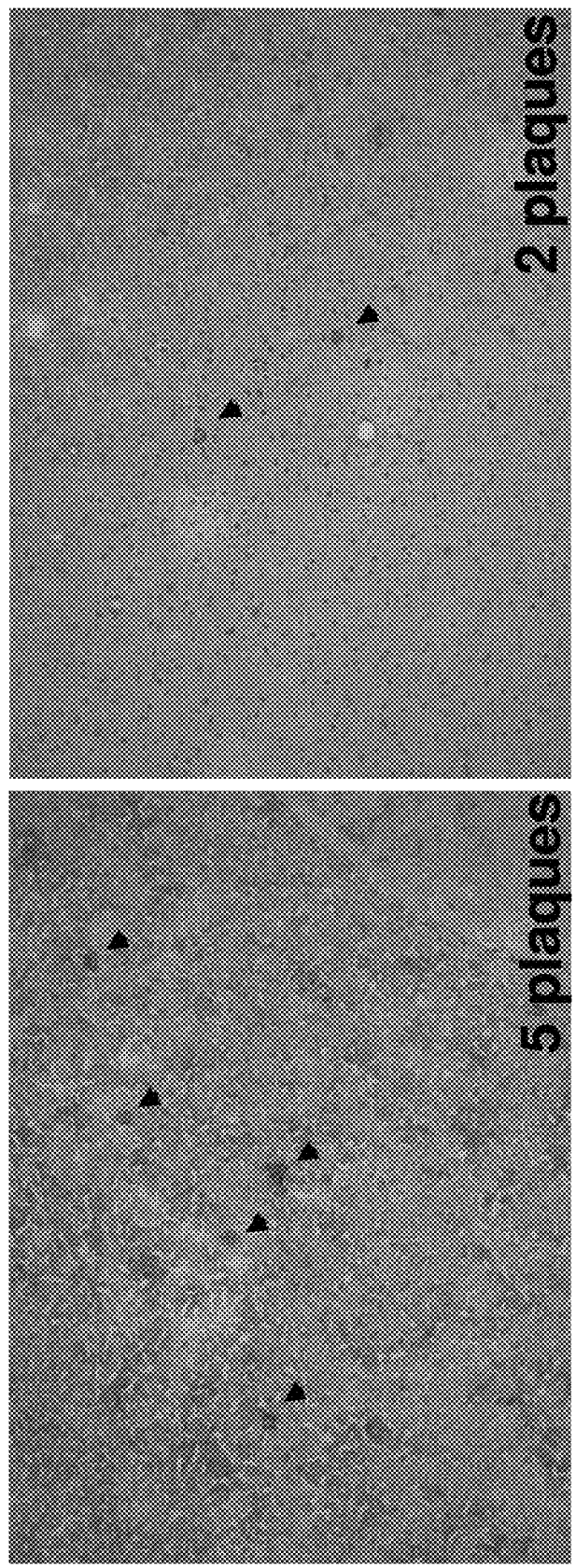
FIG. 8A-B show data from electron micrographs showing reduction in plaque numbers in a representative TgCRND8 transgenic mouse after administration of control $IgG_1$ (A) antibody in comparison to administration of 13C3 monoclonal antibodies (B).

Serial sections of cryopreserved brains from TgCRND8 mice were treated with 13C3 or IgG1 monoclonal antibodies. FIGS. 8A and 8B illustrate differences in the number of Aβ amyloid plaques between each respective antibody.

Figure 9:
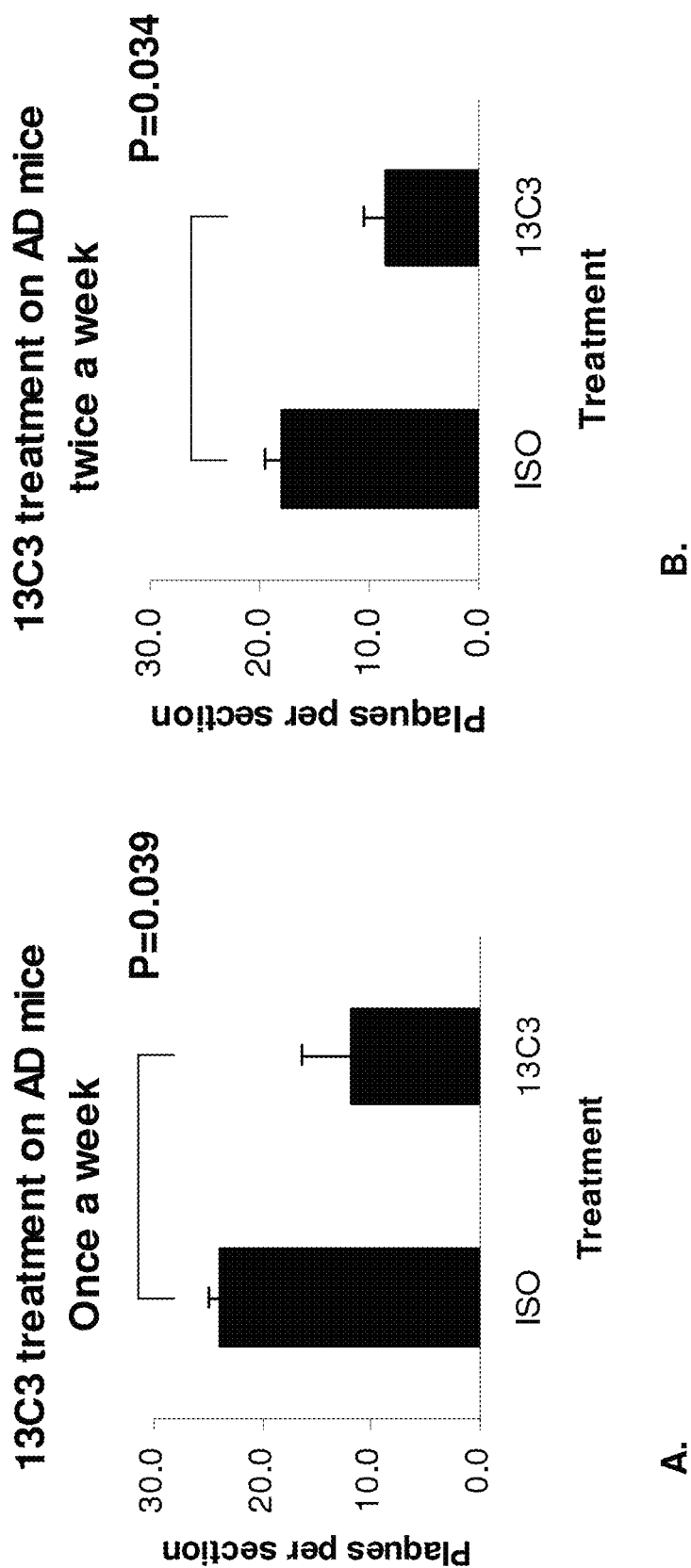
FIG. 9A-B show that treatment of TgCRND8 transgenic mice with 13C3 monoclonal antibodies on a once a week (A) or twice weekly (B) regime result in a reduction of senile plaque formation.
Figure 11A:
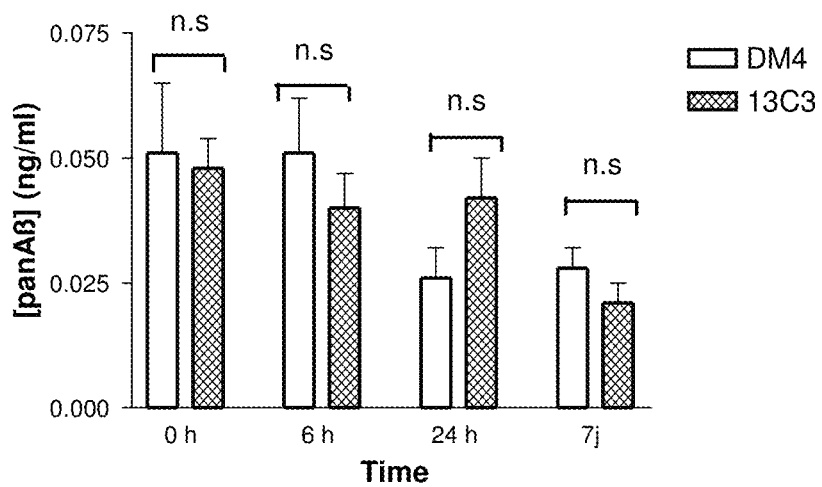
FIG. 11A-B show that the acute peripheral administration of 13C3 in APP transgenic mice (A) does not lead to an increase in plasma Aβ unlike reference antibody 3D6 administration (B).
Figure 11B:
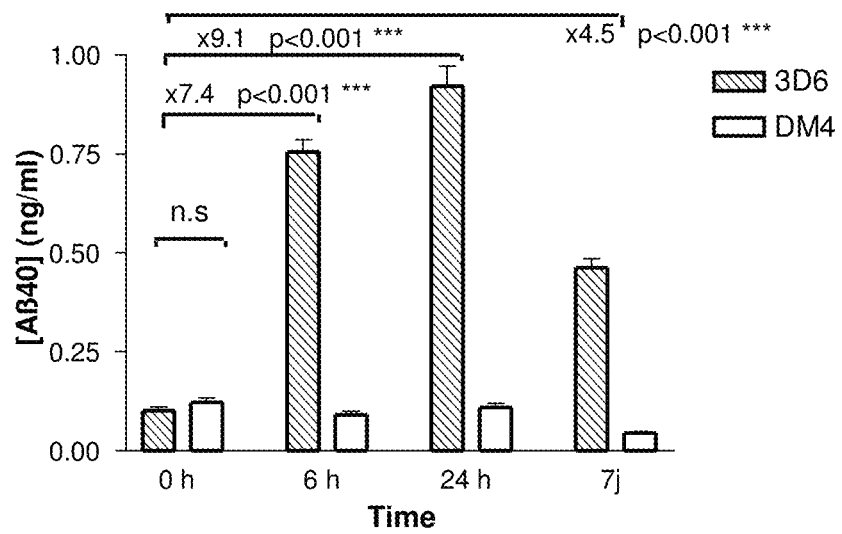

Statistical T-tests show that the 13C3 antibody treatment at once a week reduces Aβ amyloid plaques in the Alzheimer Disease model (FIG. 9A). However, twice a week treatments (FIG. 9B) show the same level of plaque reduction.

All of the above TgCRND8 mice were obtained from Dr. David Westaway of the University of Toronto.

Example 9

Molecular Characterization of the Variable Regions of MAB 13C3

Figure 10:
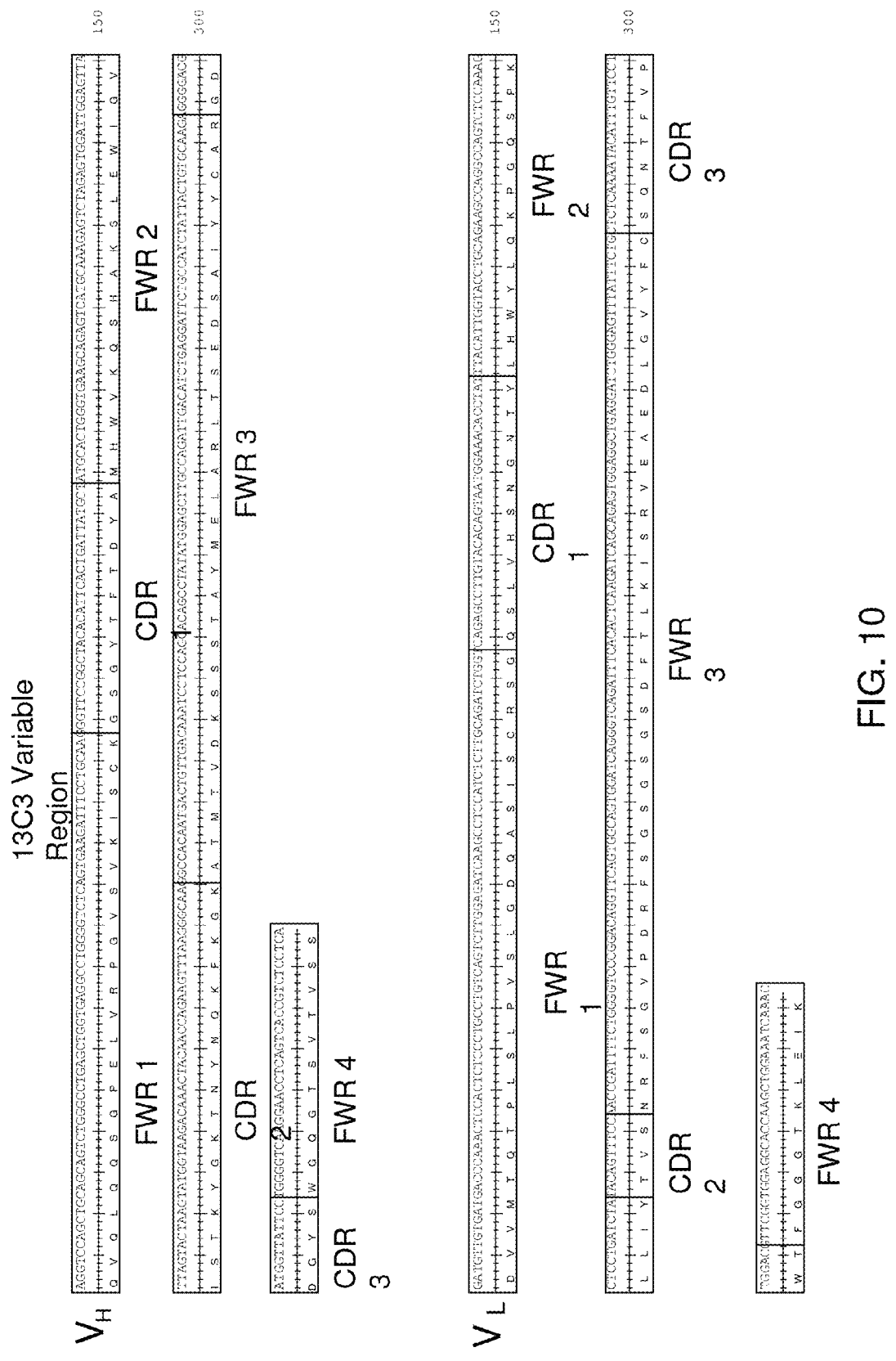

The IgG heavy chain variable region and the IgG Kappa light chain region were cloned from the 13C3 hybridoma. Both heavy and light chain sequences (FIG. 10) were analyzed using VBASE2 (http://www.vbase2.org), a database of germ-line variable genes from the immunoglobulin loci of human and mouse extracted from the EMBL-Bank and Ensembl data libraries. (Retter et al. Nucleic Acids Res. 33:D671-4 (2005)). Results for the analysis identified that both the heavy and light chain variable regions were from a newly identified immunoglobulin but had 73% and 81% identity, respectively, to other immunoglobulin variable regions in the database. Also identified in these sequences against these databases were the Frame Work Regions (FWR) and the Complementarity Determining Regions (CDR). Results were only slightly varied when sequences were analyzed against VBASE, KABAT, and IMGT/LIGM database.

Example 10

Acute Peripheral Administration of 13C3 in APP Transgenic Mice does not Lead to an Increase in Plasma as Unlike Reference Antibody 3D6 Administration APP transgenic mice (Thy APPSL, age 10-14 weeks) were injected intraperitoneally at the dose of 10 mg/kg (i.e., 300 µg/mouse) with antibodies 13C3, a control IgG1 (DM4, not recognizing Aβ) and a reference anti-Aβ antibody 3D6 recognizing all conformers of Aβ. Plasma Aβ was quantified at time zero pre-injection, 6 h, 24 h and 7 days post injection in the same mice. Quantification of plasma Aβ was performed with an immunoassay using anti-Aβ antibody pairs not interfering with 13C3 or 3D6 binding to Aβ.

Administration of 3D6, an antibody against all conformers of Aβ, leads to a large increase in plasma Aβ, likely by protecting Aβ molecules from degradation. This effect was used to suggest the potential "peripheral sink" hypothesis as mechanism of action of anti-Aβ immunotherapy (Demattos et al., 2001, PNAS 17:8850). Unlike 3D6, 13C3 administration does not lead to any increase in plasma Aβ levels. This is consistent with the properties of 13C3, an antibody that is specific for the protofibrillar forms of Aβ and is not recognizing the soluble mono- or oligomeric forms of Aβ peptide. These forms are the likely ones present in plasma.

Example 11

Figure 12:
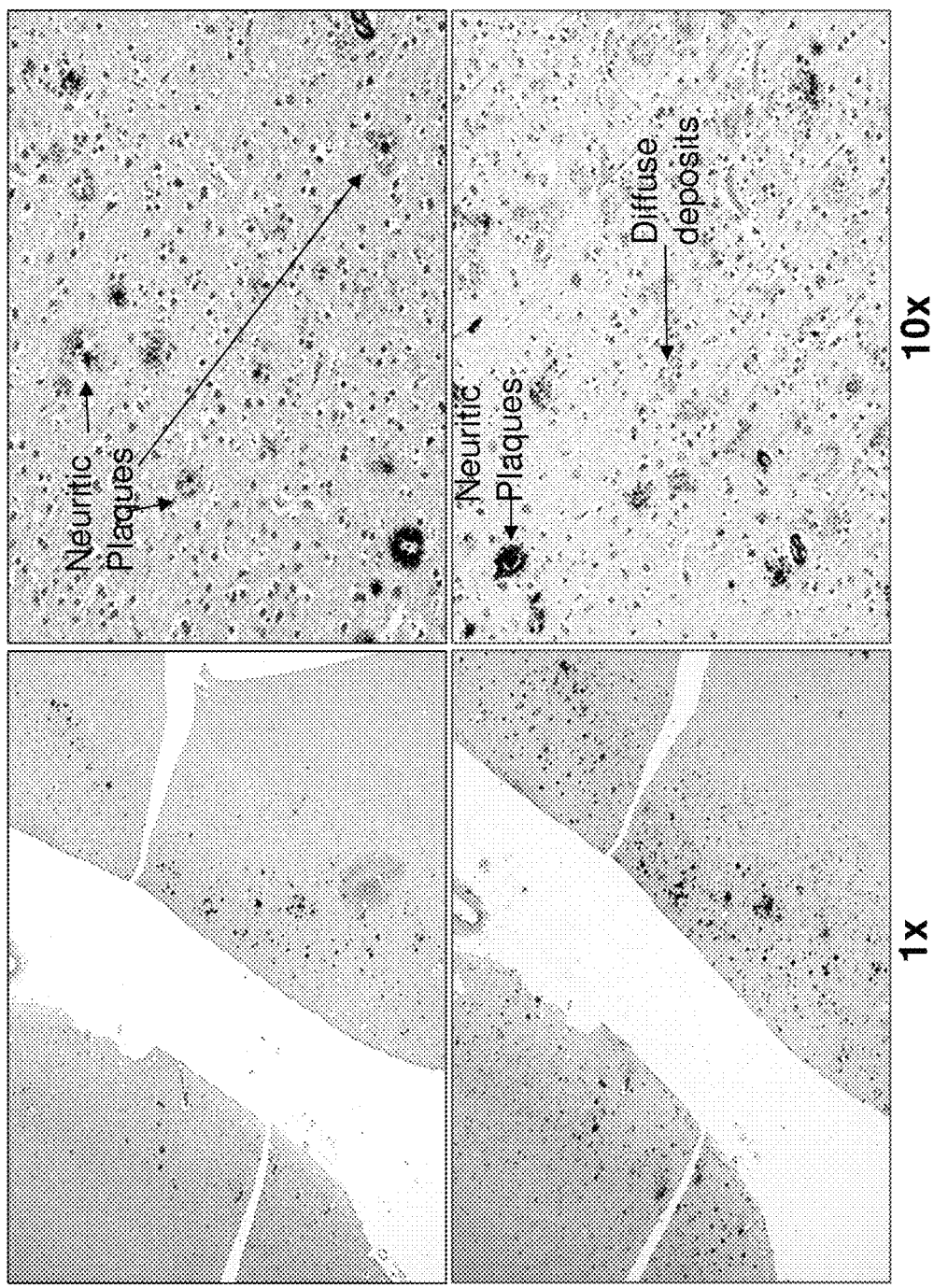
FIG. 12 shows that 13C3 recognizes human amyloid neuritic plaques (aggregated) in AD brains but not the diffuse Aβ deposits unlike the reference 3D6 anti-Aβ antibody.

13C3 Recognizes Human Amyloid Neuritic Plaques (Aggregated) in Ad Brains but not the Diffuse Aβ Deposits Unlike The Reference 3D6 Anti-Aβ Antibody Immunohistochemistry studies were performed with 13C3 and 3D6 antibodies on human Alzheimer-diagnosed brain sections using standard techniques. Antibody immunostaining was detected with a DAB chromogen (FIG. 12). 13C3 labels amyloid deposits with a typical morphology of mature amyloid neuritic plaques (also called dense plaques) with a very dense core surrounded by a lighter halo or for the larger plaques a very strong staining. In adjacent brain sections, 3D6 stains many more objects than 13C3 as seen at lower magnification (FIG. 12, left panels). Further characterization at higher magnification (FIG. 12, right panels) indicated that 3D6 labels the same mature amyloid neuritic plaques as 13C3 and, in addition, numerous diffuse amyloid deposits that have been classically described using anti-Aβ immunolabelling. The diffuse plaques are not of fibrillar nature as described in the literature as they cannot be detected by thioflavin S and other histological markers of fibrils (Mann, 1989, Ann. Med. 21:133). To rule out differences in sensitivity of the two antibodies, similar experiments were conducted with a higher concentration (20 µg/ml) of 13C3 and again diffuse deposits could not be detected. This data is consistent with the properties of 13C3, an antibody that is specific for the protofibrillar forms of Aβ and is not recognizing the soluble mono- or oligomeric forms of Aβ peptide unlike 3D6.

INDUSTRIAL APPLICABILITY

The invention has applications in the treatment and diagnosis of Alzheimer's disease.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What claimed is:

1. An isolated antibody, or an antigen binding fragment thereof, that specifically interacts and shows a measurable affinity to a conformational epitope of a protofibril form of Aβ peptide, whereby the protofibril epitope is represented by an exposed region of a Aβ-protofibril form comprising the amino acid sequence as set forth in SEQ ID NO:2, wherein said antibody is a chimeric or humanized monoclonal antibody and shows minimal or no affinity for monomer or dimer forms of Aβ peptide, and is capable of detecting a peptide comprising amino acids 4-12 of SEQ ID NO: 2, and wherein the antibody or antigen binding fragment comprises (1) a variable light chain comprised of the amino acid sequence as set forth in SEQ ID NO:5 or a variable heavy chain comprised of the amino acid sequence as set forth in SEQ ID NO:7; or (2) a variable light chain comprising a CDR1 region as set forth in SEQ ID NO: 13, a CDR2 region as set forth in SEQ ID NO: 14, and a CDR3 as set forth in SEQ ID NO: 15, and a variable heavy chain comprised of a CDR1 region as set forth in SEQ ID NO:20, a CDR2 region as set forth in SEQ ID NO:21, and a CDR3 as set forth in SEQ ID NO:22.

2. The isolated antibody or antigen binding fragment of claim 1, that specifically interacts and shows a measurable affinity to a conformational epitope of a protofibril form of Aβ peptide, whereby wherein the protofibril epitope is represented by an exposed region of a Aβ-protofibril form comprising an amino acid sequence selected from the group consisting of SEQ ID NO:3 and SEQ ID NO:4, wherein said antibody is a humanized monoclonal antibody and shows minimal or no affinity for monomer or dimer forms of Aβ peptide.

3. The antibody or antigen binding fragment of claim 2 comprising said variable light chain comprised of the amino acid sequence as set forth in SEQ ID NO:5 or said variable heavy chain comprised of the amino acid sequence as set forth in SEQ ID NO:7.

4. The antibody or antigen binding fragment of claim 1 wherein the antibody is a humanized monoclonal antibody.

5. The antibody or antigen binding fragment of claim 1 wherein the antibody is a chimeric antibody.

6. The isolated antibody, or an antigen binding fragment thereof, of claim 1 comprising the amino acid sequence set forth in SEQ ID NO:7 and the amino acid sequence set forth in SEQ ID NO:5.

7. The isolated antibody, or an antigen binding fragment thereof, of claim 1 comprising (i) a variable light chain comprising a CDR1 region as set forth in SEQ ID NO: 13, a CDR2 region as set forth in SEQ ID NO: 14, and a CDR3 as set forth in SEQ ID NO: 15, and (ii) a variable heavy chain comprised of a CDR1 region as set forth in SEQ ID NO:20, a CDR2 region as set forth in SEQ ID NO:21, and a CDR3 as set forth in SEQ ID NO:22.

8. A kit for detecting protofibril form of β-amyloid peptide while showing minimal affinity to low molecular weight forms of β-amyloid peptide, comprising:

(a) the antibody of claim 1 or a fragment thereof, capable of specifically binding in vitro to a repeating conformational epitope of a protofibril form of β-amyloid peptide while showing minimal affinity to low molecular weight forms of β-amyloid peptide; and, (b) a reagent that binds, directly, or indirectly, to said antibody or the fragment thereof.

9. A pharmaceutical composition comprising the antibody or antigen binding fragment of claim 1, which specifically interacts with the protofibrillar form of β-amyloid, wherein said specific interaction is characterized by a ratio of the affinity of said variable region fragment for the protofibrillar Aβ form to the affinity for other Aβ forms greater than about 2.

10. An isolated nucleic acid molecule encoding a variable chain fragment of an isolated antibody, or an antigen binding fragment thereof, of claim 1.

11. The isolated nucleic acid molecule of claim 10, wherein the nucleic acid molecule comprises the nucleotide sequence as set for in SEQ ID NO:8 or 6.

12. An expression vector comprising the nucleic acid molecule of claim 11.

13. A host cell comprising the expression vector of claim 12.

14. A hybridoma deposited under ATCC Accession No. PTA-8830.

15. An antibody or antigen binding fragment thereof wherein the antibody is designated 13C3 and produced by the hybridoma of claim 14.

16. A method for quantifying the amount of a protofibril form of β-amyloid peptide in a tissue or fluid sample, comprising:

(a) obtaining the tissue or fluid sample from a subject;
(b) contacting the tissue or fluid sample with the antibody of claim 1 or fragment thereof that specifically binds to the protofibril form of β-amyloid peptide while showing minimal affinity to low molecular weight forms of β-amyloid peptide; and,
(c) quantifying the amount of protofibril form of β-amyloid peptide in the sample.

17. A method of inhibiting deposition of β-amyloid fiber plaques within a mammal which comprises administering to the mammal pharmaceutically effective amount of the antibody or antigen binding fragment of claim 1 which specifically interacts with the protofibril form of β-amyloid peptide so as to inhibit formation and deposition of β-amyloid fiber plaques.

* * * * *

SEQUENCE LISTING

```
<160> NUMBER OF SEQ ID NOS: 52

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15
```

```
Leu Val Phe Phe Ala Glu Asp Val Gly Ser Asn Lys Gly Ala Ile Ile
                 20                  25                  30

Gly Leu Met Val Gly Gly Val Val Ile Ala
        35                  40

<210> SEQ ID NO 2
<211> LENGTH: 20
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe
            20

<210> SEQ ID NO 3
<211> LENGTH: 9
<212> TYPE: PRT
<213> ORGANISM: Homo sapiens

<400> SEQUENCE: 3

Phe Arg His Asp Ser Gly Tyr Glu Val
1               5

<210> SEQ ID NO 4
<211> LENGTH: 12
<212> TYPE: PRT
<213> ORGANISM: Homo sapiens

<400> SEQUENCE: 4

Gly Tyr Glu Val His His Gln Lys Leu Val Phe Phe
1               5                   10

<210> SEQ ID NO 5
<211> LENGTH: 113
<212> TYPE: PRT
<213> ORGANISM: Mus musculus

<400> SEQUENCE: 5

Asp Val Val Met Thr Gln Thr Pro Leu Ser Leu Pro Val Ser Leu Gly
1               5                   10                  15

Asp Gln Ala Ser Ile Ser Cys Arg Ser Gly Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr Phe Val Pro Trp Thr Phe Gly Gly Gly Thr Lys Leu Glu Ile Lys
            100                 105                 110

Arg

<210> SEQ ID NO 6
<211> LENGTH: 339
<212> TYPE: DNA
<213> ORGANISM: Mus musculus
```

<400> SEQUENCE: 6

```
gatgttgtga tgacccaaac tccactctcc ctgcctgtca gtcttggaga tcaagcctcc    60
atctcttgca gatctggtca gagccttgta cacagtaatg gaaacaccta tttacattgg   120
tacctgcaga agccaggcca gtctccaaag ctcctgatct atacagtttc caaccgattt   180
tctggggtcc cggacaggtt cagtggcagt ggatcagggt cagatttcac actcaagatc   240
agcagagtgg aggctgagga tctgggagtt tatttctgct ctcaaaatac atttgttcct   300
tggacgttcg gtggaggcac caagctggaa atcaaacgg                          339
```

<210> SEQ ID NO 7
<211> LENGTH: 115
<212> TYPE: PRT
<213> ORGANISM: Mus musculus

<400> SEQUENCE: 7

```
Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Val Ile Ser Thr Lys Tyr Gly Lys Thr Asn Tyr Asn Gln Lys Phe
    50                  55                  60

Lys Gly Lys Ala Thr Met Thr Val Asp Lys Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Gly Asp Asp Gly Tyr Ser Trp Gly Gln Gly Thr Ser Val Thr
            100                 105                 110

Val Ser Ser
        115
```

<210> SEQ ID NO 8
<211> LENGTH: 345
<212> TYPE: DNA
<213> ORGANISM: Mus musculus

<400> SEQUENCE: 8

```
caggtccagc tgcagcagtc tgggcctgag ctggtgaggc ctggggtctc agtgaagatt    60
tcctgcaagg gttccggcta cacattcact gattatgcta tgcactgggt gaagcagagt   120
catgcaaaga gtctagagtg gattggagtt attagtacta agtatggtaa gacaaactac   180
aaccagaagt ttaagggcaa ggccacaatg actgttgaca atcctccag cacagcctat   240 atggagcttg ccagattgac atctgaggat tctgccatct attactgtgc aagaggggac   300
gatggttatt cctgggggtca aggaacctca gtcaccgtct cctca                  345
```

<210> SEQ ID NO 9
<211> LENGTH: 26
<212> TYPE: PRT
<213> ORGANISM: Mus musculus

<400> SEQUENCE: 9

```
Asp Val Val Met Thr Gln Thr Pro Leu Ser Leu Pro Val Ser Leu Gly
1               5                   10                  15

Asp Gln Ala Ser Ile Ser Cys Arg Ser Gly
            20                  25
```

```
<210> SEQ ID NO 10
<211> LENGTH: 17
<212> TYPE: PRT
<213> ORGANISM: Mus musculus

<400> SEQUENCE: 10

Leu His Trp Tyr Leu Gln Lys Pro Gly Gln Ser Pro Lys Leu Leu Ile
1               5                   10                  15

Tyr

<210> SEQ ID NO 11
<211> LENGTH: 36
<212> TYPE: PRT
<213> ORGANISM: Mus musculus

<400> SEQUENCE: 11

Asn Arg Phe Ser Gly Val Pro Asp Arg Phe Ser Gly Ser Gly Ser Gly
1               5                   10                  15

Ser Asp Phe Thr Leu Lys Ile Ser Arg Val Glu Ala Glu Asp Leu Gly
            20                  25                  30

Val Tyr Phe Cys
            35

<210> SEQ ID NO 12
<211> LENGTH: 11
<212> TYPE: PRT
<213> ORGANISM: Mus musculus

<400> SEQUENCE: 12

Phe Gly Gly Gly Thr Lys Leu Glu Ile Lys Arg
1               5                   10

<210> SEQ ID NO 13
<211> LENGTH: 11
<212> TYPE: PRT
<213> ORGANISM: Mus musculus

<400> SEQUENCE: 13

Gln Ser Leu Val His Ser Asn Gly Asn Thr Tyr
1               5                   10

<210> SEQ ID NO 14
<211> LENGTH: 3
<212> TYPE: PRT
<213> ORGANISM: Mus musculus

<400> SEQUENCE: 14

Thr Val Ser
1

<210> SEQ ID NO 15
<211> LENGTH: 9
<212> TYPE: PRT
<213> ORGANISM: Mus musculus

<400> SEQUENCE: 15

Ser Gln Asn Thr Phe Val Pro Trp Thr
1               5

<210> SEQ ID NO 16
<211> LENGTH: 23
<212> TYPE: PRT
```

```
<213> ORGANISM: Mus musculus

<400> SEQUENCE: 16

Gln Val Gln Leu Gln Gln Ser Gly Pro Glu Leu Val Arg Pro Gly Val
1               5                   10                  15

Ser Val Lys Ile Ser Cys Lys
            20

<210> SEQ ID NO 17
<211> LENGTH: 17
<212> TYPE: PRT
<213> ORGANISM: Mus musculus

<400> SEQUENCE: 17

Met His Trp Val Lys Gln Ser His Ala Lys Ser Leu Glu Trp Ile Gly
1               5                   10                  15

Val

<210> SEQ ID NO 18
<211> LENGTH: 31
<212> TYPE: PRT
<213> ORGANISM: Artificial
<220> FEATURE:
<223> OTHER INFORMATION: a variable heavy region for the isolated 13C3
      or 13C3-like antibodies

<400> SEQUENCE: 18

Ala Thr Met Thr Val Asp Lys Ser Ser Ser Thr Ala Tyr Met Glu Leu
1               5                   10                  15

Ala Arg Leu Thr Ser Glu Asp Ser Ala Ile Tyr Tyr Cys Ala Arg
            20                  25                  30

<210> SEQ ID NO 19
<211> LENGTH: 11
<212> TYPE: PRT
<213> ORGANISM: Mus musculus

<400> SEQUENCE: 19

Trp Gly Gln Gly Thr Ser Val Thr Val Ser Ser
1               5                   10

<210> SEQ ID NO 20
<211> LENGTH: 10
<212> TYPE: PRT
<213> ORGANISM: Mus musculus

<400> SEQUENCE: 20

Gly Ser Gly Tyr Thr Phe Thr Asp Tyr Ala
1               5                   10

<210> SEQ ID NO 21
<211> LENGTH: 17
<212> TYPE: PRT
<213> ORGANISM: Mus musculus

<400> SEQUENCE: 21

Ile Ser Thr Lys Tyr Gly Lys Thr Asn Tyr Asn Gln Lys Phe Lys Gly
1               5                   10                  15

Lys

<210> SEQ ID NO 22
<211> LENGTH: 6
<212> TYPE: PRT
```

<213> ORGANISM: Mus musculus

<400> SEQUENCE: 22

Gly Asp Asp Gly Tyr Ser
1               5

<210> SEQ ID NO 23
<211> LENGTH: 13
<212> TYPE: PRT
<213> ORGANISM: Homo sapiens

<400> SEQUENCE: 23

Asp Ala Glu Phe Arg His Asp Ser Gly Tyr Glu Val His
1               5                   10

<210> SEQ ID NO 24
<211> LENGTH: 13
<212> TYPE: PRT
<213> ORGANISM: Homo sapiens

<400> SEQUENCE: 24

Ala Glu Phe Arg His Asp Ser Gly Tyr Glu Val His His
1               5                   10

<210> SEQ ID NO 25
<211> LENGTH: 13
<212> TYPE: PRT
<213> ORGANISM: Homo sapiens

<400> SEQUENCE: 25

Glu Phe Arg His Asp Ser Gly Tyr Glu Val His His Gln
1               5                   10

<210> SEQ ID NO 26
<211> LENGTH: 13
<212> TYPE: PRT
<213> ORGANISM: Homo sapiens

<400> SEQUENCE: 26

Phe Arg His Asp Ser Gly Tyr Glu Val His His Gln Lys
1               5                   10

<210> SEQ ID NO 27
<211> LENGTH: 13
<212> TYPE: PRT
<213> ORGANISM: Homo sapiens

<400> SEQUENCE: 27

Arg His Asp Ser Gly Tyr Glu Val His His Gln Lys Leu
1               5                   10

<210> SEQ ID NO 28
<211> LENGTH: 13
<212> TYPE: PRT
<213> ORGANISM: Homo sapiens

<400> SEQUENCE: 28

His Asp Ser Gly Tyr Glu Val His His Gln Lys Leu Val
1               5                   10

<210> SEQ ID NO 29
<211> LENGTH: 13
<212> TYPE: PRT
<213> ORGANISM: Homo sapiens

<400> SEQUENCE: 29

Asp Ser Gly Tyr Glu Val His His Gln Lys Leu Val Phe
1               5                   10

<210> SEQ ID NO 30
<211> LENGTH: 13
<212> TYPE: PRT
<213> ORGANISM: Homo sapiens

<400> SEQUENCE: 30

Ser Gly Tyr Glu Val His His Gln Lys Leu Val Phe Phe
1               5                   10

<210> SEQ ID NO 31
<211> LENGTH: 13
<212> TYPE: PRT
<213> ORGANISM: Homo sapiens

<400> SEQUENCE: 31

Gly Tyr Glu Val His His Gln Lys Leu Val Phe Phe Ala
1               5                   10

<210> SEQ ID NO 32
<211> LENGTH: 13
<212> TYPE: PRT
<213> ORGANISM: Homo sapiens

<400> SEQUENCE: 32

Tyr Glu Val His His Gln Lys Leu Val Phe Phe Ala Glu
1               5                   10

<210> SEQ ID NO 33
<211> LENGTH: 13
<212> TYPE: PRT
<213> ORGANISM: Homo sapiens

<400> SEQUENCE: 33

Glu Val His His Gln Lys Leu Val Phe Phe Ala Glu Asp
1               5                   10

<210> SEQ ID NO 34
<211> LENGTH: 13
<212> TYPE: PRT
<213> ORGANISM: Homo sapiens

<400> SEQUENCE: 34

Val His His Gln Lys Leu Val Phe Phe Ala Glu Asp Val
1               5                   10

<210> SEQ ID NO 35
<211> LENGTH: 13
<212> TYPE: PRT
<213> ORGANISM: Homo sapiens

<400> SEQUENCE: 35

His His Gln Lys Leu Val Phe Phe Ala Glu Asp Val Gly
1               5                   10

<210> SEQ ID NO 36
<211> LENGTH: 13
<212> TYPE: PRT
<213> ORGANISM: Homo sapiens

<400> SEQUENCE: 36

His Gln Lys Leu Val Phe Phe Ala Glu Asp Val Gly Ser
1               5                   10

<210> SEQ ID NO 37
<211> LENGTH: 13
<212> TYPE: PRT
<213> ORGANISM: Homo sapiens

<400> SEQUENCE: 37

Gln Lys Leu Val Phe Phe Ala Glu Asp Val Gly Ser Asn
1               5                   10

<210> SEQ ID NO 38
<211> LENGTH: 13
<212> TYPE: PRT
<213> ORGANISM: Homo sapiens

<400> SEQUENCE: 38

Lys Leu Val Phe Phe Ala Glu Asp Val Gly Ser Asn Lys
1               5                   10

<210> SEQ ID NO 39
<211> LENGTH: 13
<212> TYPE: PRT
<213> ORGANISM: Homo sapiens

<400> SEQUENCE: 39

Leu Val Phe Phe Ala Glu Asp Val Gly Ser Asn Lys Gly
1               5                   10

<210> SEQ ID NO 40
<211> LENGTH: 13
<212> TYPE: PRT
<213> ORGANISM: Homo sapiens

<400> SEQUENCE: 40

Val Phe Phe Ala Glu Asp Val Gly Ser Asn Lys Gly Ala
1               5                   10

<210> SEQ ID NO 41
<211> LENGTH: 13
<212> TYPE: PRT
<213> ORGANISM: Homo sapiens

<400> SEQUENCE: 41

Phe Phe Ala Glu Asp Val Gly Ser Asn Lys Gly Ala Ile
1               5                   10

<210> SEQ ID NO 42
<211> LENGTH: 13
<212> TYPE: PRT
<213> ORGANISM: Homo sapiens

<400> SEQUENCE: 42

Phe Ala Glu Asp Val Gly Ser Asn Lys Gly Ala Ile Ile
1               5                   10

<210> SEQ ID NO 43
<211> LENGTH: 13
<212> TYPE: PRT
<213> ORGANISM: Homo sapiens

<400> SEQUENCE: 43

Ala Glu Asp Val Gly Ser Asn Lys Gly Ala Ile Ile Gly
1               5                   10

<210> SEQ ID NO 44
<211> LENGTH: 13
<212> TYPE: PRT
<213> ORGANISM: Homo sapiens

<400> SEQUENCE: 44

Glu Asp Val Gly Ser Asn Lys Gly Ala Ile Ile Gly Leu
1               5                   10

<210> SEQ ID NO 45
<211> LENGTH: 13
<212> TYPE: PRT
<213> ORGANISM: Homo sapiens

<400> SEQUENCE: 45

Asp Val Gly Ser Asn Lys Gly Ala Ile Ile Gly Leu Met
1               5                   10

<210> SEQ ID NO 46
<211> LENGTH: 13
<212> TYPE: PRT
<213> ORGANISM: Homo sapiens

<400> SEQUENCE: 46

Val Gly Ser Asn Lys Gly Ala Ile Ile Gly Leu Met Val
1               5                   10

<210> SEQ ID NO 47
<211> LENGTH: 13
<212> TYPE: PRT
<213> ORGANISM: Homo sapiens

<400> SEQUENCE: 47

Gly Ser Asn Lys Gly Ala Ile Ile Gly Leu Met Val Gly
1               5                   10

<210> SEQ ID NO 48
<211> LENGTH: 13
<212> TYPE: PRT
<213> ORGANISM: Homo sapiens

<400> SEQUENCE: 48

Ser Asn Lys Gly Ala Ile Ile Gly Leu Met Val Gly Gly
1               5                   10

<210> SEQ ID NO 49
<211> LENGTH: 13
<212> TYPE: PRT
<213> ORGANISM: Homo sapiens

<400> SEQUENCE: 49

Asn Lys Gly Ala Ile Ile Gly Leu Met Val Gly Gly Val
1               5                   10

<210> SEQ ID NO 50
<211> LENGTH: 13
<212> TYPE: PRT
<213> ORGANISM: Homo sapiens

<400> SEQUENCE: 50

Lys Gly Ala Ile Ile Gly Leu Met Val Gly Gly Val Val
1               5                   10

```
<210> SEQ ID NO 51
<211> LENGTH: 13
<212> TYPE: PRT
<213> ORGANISM: Homo sapiens

<400> SEQUENCE: 51

Gly Ala Ile Ile Gly Leu Met Val Gly Gly Val Val Ile
1               5                   10

<210> SEQ ID NO 52
<211> LENGTH: 13
<212> TYPE: PRT
<213> ORGANISM: Homo sapiens

<400> SEQUENCE: 52

Ala Ile Ile Gly Leu Met Val Gly Gly Val Val Ile Ala
1               5                   10
```